(12) United States Patent
Feldman et al.

(10) Patent No.: US 12,198,000 B2
(45) Date of Patent: *Jan. 14, 2025

(54) IDENTITY VERIFYING DEVICE AND METHODS

(71) Applicant: Fund for Medical Research Development of Infrastructure & Health Services by Barzilai Medical Center, Ashkelon (IL)

(72) Inventors: Arie Feldman, Ashkelon (IL); David Gales, Ashkelon (IL)

(73) Assignee: Fund for Medical Research Development of Infrastructure & Health Services by Barzilal Medical Center, Ashkolon (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/135,196

(22) Filed: Apr. 17, 2023

(65) Prior Publication Data

US 2023/0252254 A1    Aug. 10, 2023

Related U.S. Application Data

(63) Continuation of application No. 17/433,667, filed as application No. PCT/IL2020/050205 on Feb. 24, 2020, now Pat. No. 11,630,969.

(Continued)

(51) Int. Cl.
*G16H 40/40* (2018.01)
*B41K 1/00* (2006.01)
(Continued)

(52) U.S. Cl.
CPC ............ *G06K 7/1439* (2013.01); *B41K 1/003* (2013.01); *G06V 40/1318* (2022.01); *G06V 40/1365* (2022.01); *G16H 40/40* (2018.01)

(58) Field of Classification Search
CPC ........ G06K 7/1439; B41K 1/003; B41K 1/36; G06V 40/1318; G06V 40/1365; G16H 40/40; A61B 5/117; A61B 90/96
See application file for complete search history.

(56) References Cited

U.S. PATENT DOCUMENTS

| 3,848,112 A | 11/1974 | Weichselbaum et al. |
| 4,122,947 A | 10/1978 | Falla |

(Continued)

FOREIGN PATENT DOCUMENTS

| CN | 108859451 | 11/2018 |
| WO | WO 2006/053316 | 5/2006 |
| WO | WO 2020/174463 | 9/2020 |

OTHER PUBLICATIONS

International Preliminary Report on Patentability Dated Jun. 3, 2021 From the International Preliminary Examining Authority Re. Application No. PCT/IL2020/050205. (14 Pages).

(Continued)

*Primary Examiner* — Tuyen K Vo

(57) ABSTRACT

A method for identity (ID) verification, including:

acquiring one or more ID indications of at least one item using a handheld verifying device;

automatically verifying by the verifying device a desired relation between the one or more acquired ID indications and stored verification data associated with the verifying device;

physically marking the item using the verifying device with a verifying marking if the desired relation is automatically verified.

20 Claims, 19 Drawing Sheets

Related U.S. Application Data

(60) Provisional application No. 62/809,764, filed on Feb. 25, 2019.

(51) Int. Cl.
  G06K 7/14 (2006.01)
  G06V 40/12 (2022.01)
  G06V 40/13 (2022.01)

(56) References Cited

U.S. PATENT DOCUMENTS

| | | | |
|---|---|---|---|
| 4,476,381 A | 10/1984 | Rubin | |
| 4,857,716 A | 8/1989 | Gombrich et al. | |
| 8,308,640 B2 | 11/2012 | Baldus et al. | |
| 2003/0009244 A1 | 1/2003 | Engleson et al. | |
| 2003/0055685 A1* | 3/2003 | Cobb | G16H 20/17 705/3 |
| 2006/0180659 A1 | 8/2006 | Loffredo et al. | |
| 2011/0196306 A1* | 8/2011 | De La Huerga | A61M 5/16827 604/93.01 |
| 2012/0025981 A1* | 2/2012 | Marcovici | B65D 83/04 221/199 |
| 2012/0075397 A1 | 3/2012 | Mistyurik et al. | |
| 2013/0240624 A1 | 9/2013 | Baym et al. | |
| 2013/0270339 A1* | 10/2013 | Westra | G06F 16/20 235/375 |
| 2015/0332209 A1* | 11/2015 | DeBusk | G06K 19/07758 705/2 |
| 2016/0292386 A1* | 10/2016 | Finkelstein | G16H 10/60 |
| 2016/0350168 A1 | 12/2016 | Chen et al. | |
| 2017/0341446 A1 | 11/2017 | Almutairi | |
| 2018/0319186 A1 | 11/2018 | Zhu et al. | |
| 2019/0090954 A1 | 3/2019 | Kotian et al. | |
| 2020/0026893 A1* | 1/2020 | Mukhopadhyaya | G06K 7/10297 |
| 2021/0257070 A1* | 8/2021 | Khajavi | G16H 20/40 |
| 2022/0138447 A1 | 5/2022 | Feldman et al. | |

OTHER PUBLICATIONS

International Search Report and the Written Opinion Dated May 21, 2020 From the International Searching Authority Re. Application No. PCT/IL2020/050205. (10 Pages).

Notice of Allowance Dated Jan. 24, 2023 from the US Patent and Trademark Office Re. U.S. Appl. No. 17/433,667. (11 pages).

Supplementary European Search Report Dated Nov. 11, 2022 From the European Patent Office Re. Application No. 20763927.9 (5 pages).

* cited by examiner

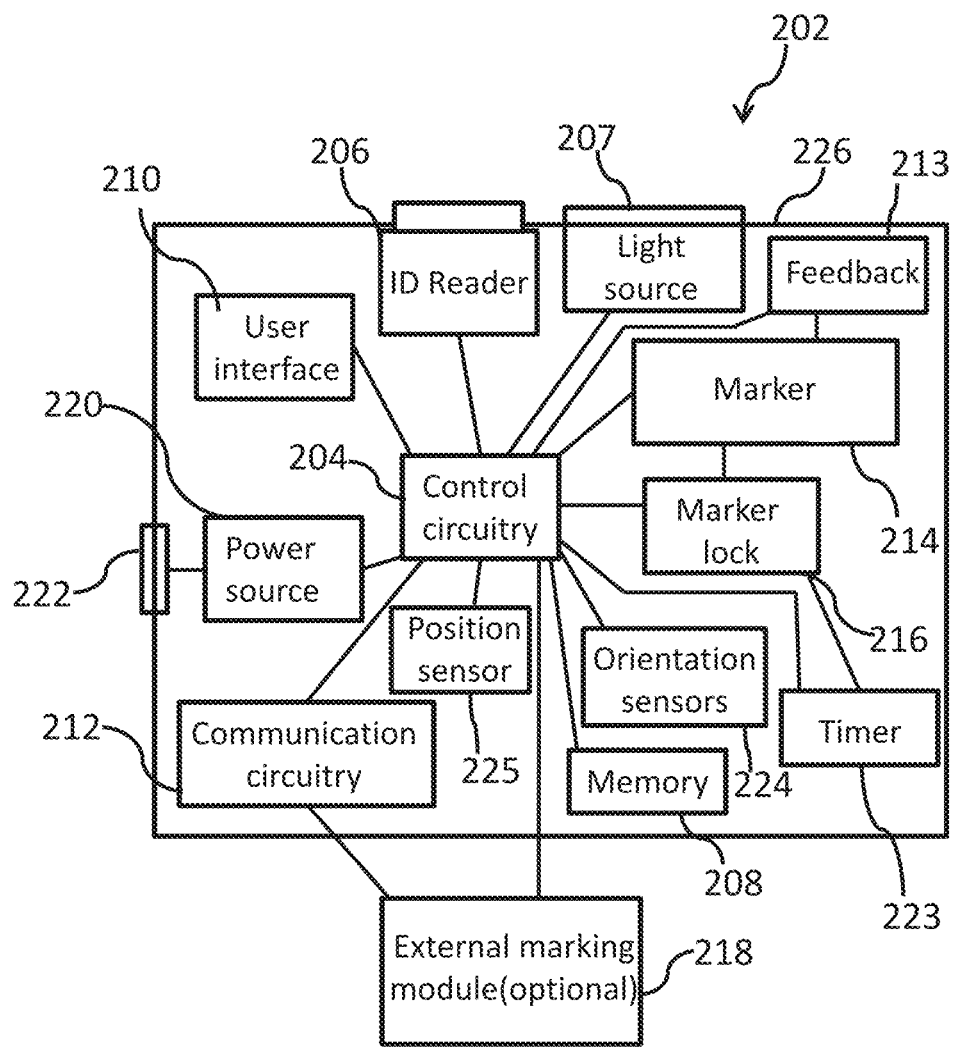

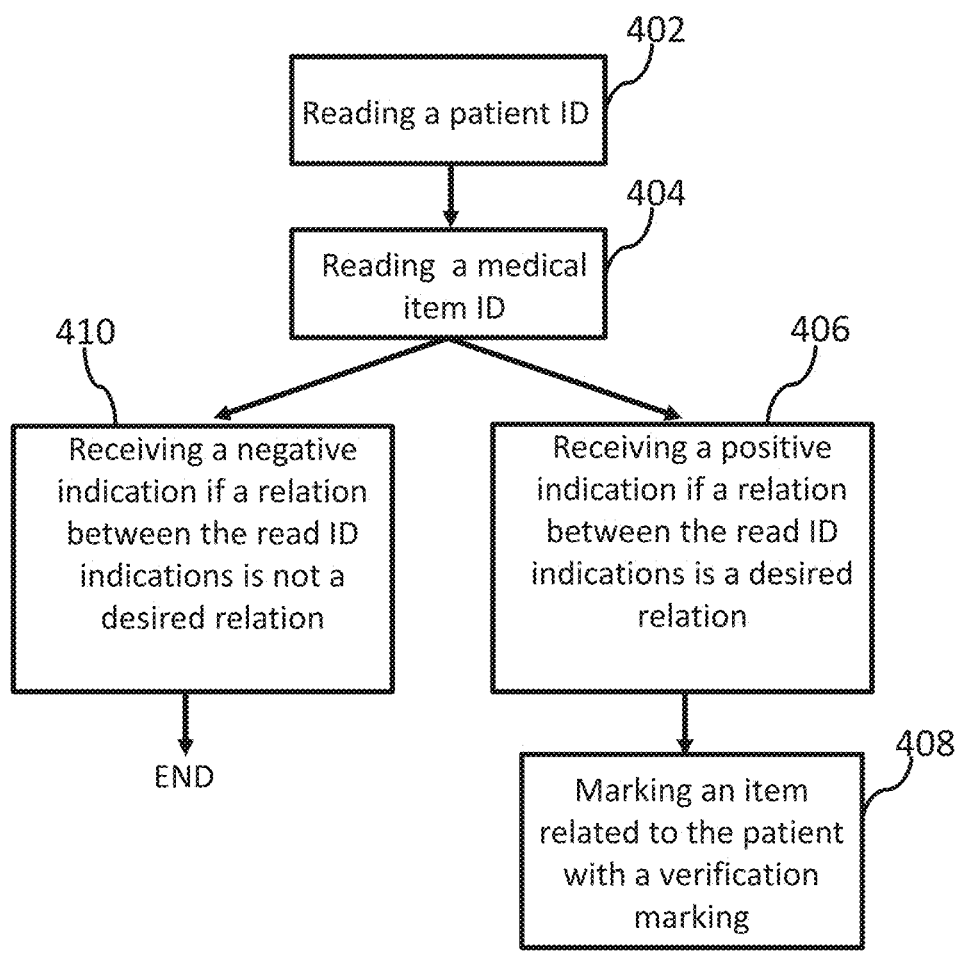

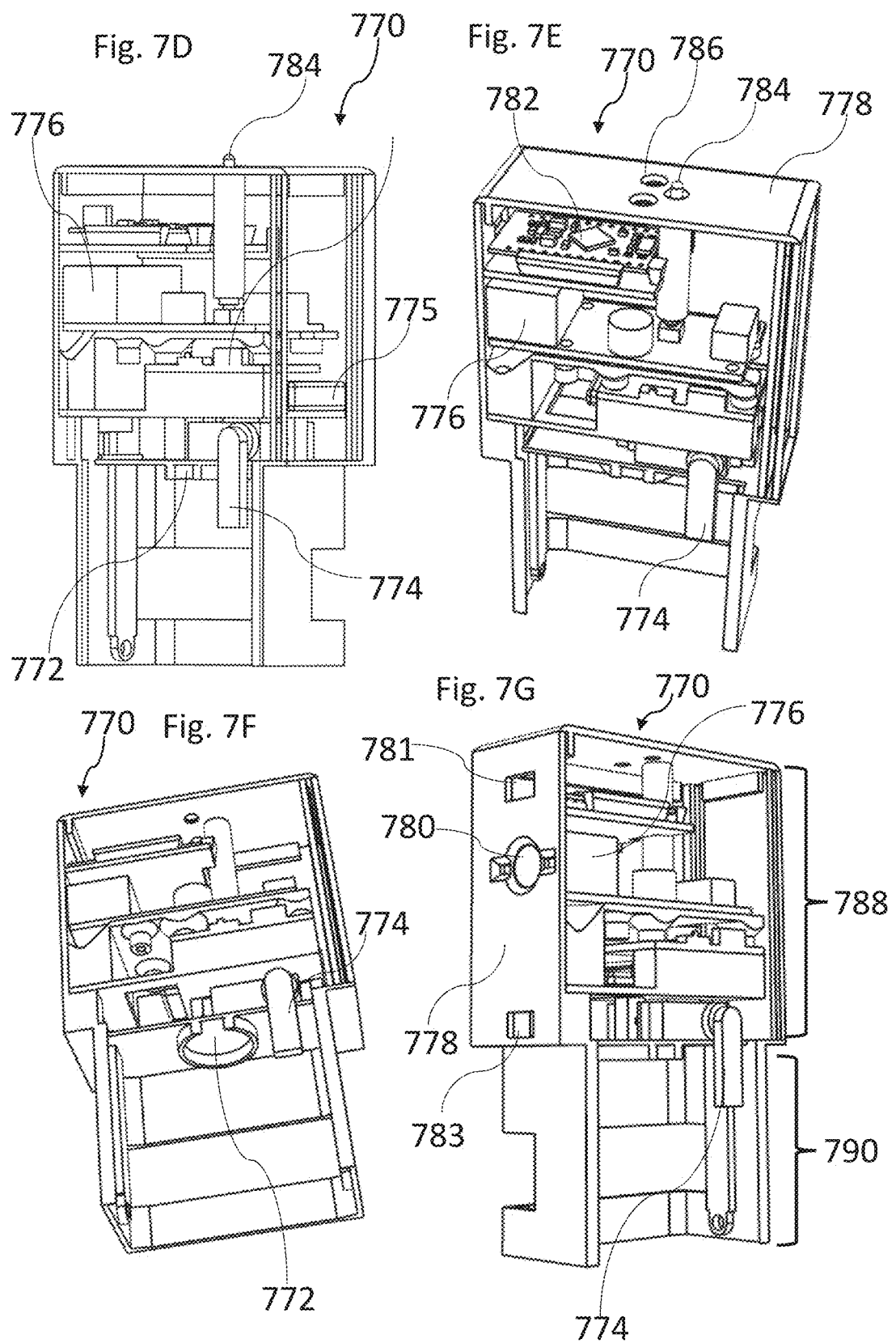

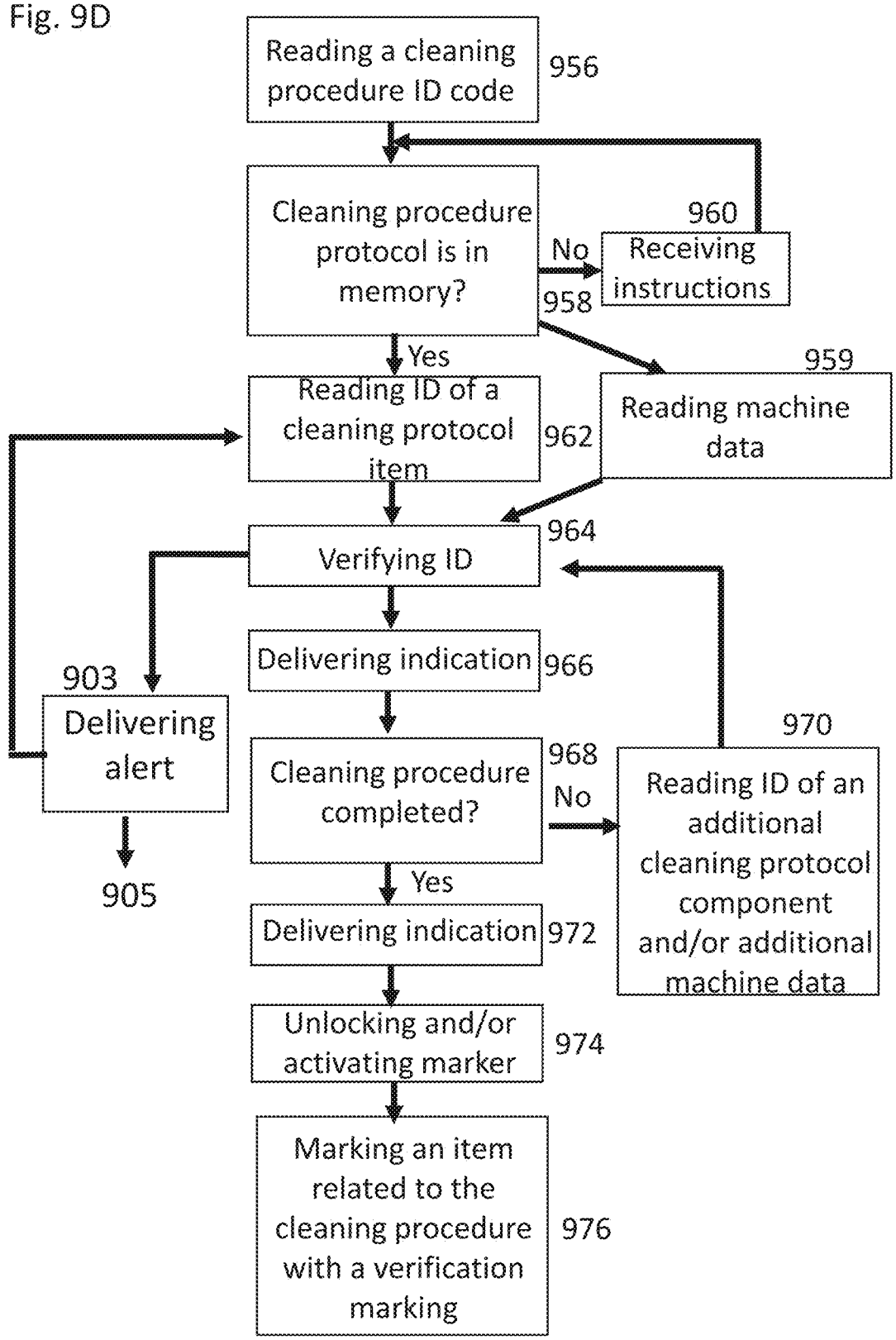

IDENTITY VERIFYING DEVICE AND METHODS

RELATED APPLICATIONS

This application is a continuation of U.S. patent application Ser. No. 17/433,667 filed on Aug. 25, 2021, which is a National Phase of PCT Patent Application No. PCT/IL2020/050205 having International filing date of Feb. 24, 2020, which claims the benefit of priority under 35 USC § 119(e) of U.S. Provisional Patent Application No. 62/809,764 filed on Feb. 25, 2019. The contents of the above applications are all incorporated by reference as if fully set forth herein in their entirety.

FIELD AND BACKGROUND OF THE INVENTION

The present invention, in some embodiments thereof, relates to identity verification and, more particularly, but not exclusively, to identity verification of medical objects.

U.S. Pat. No. 4,857,716 describes "a patient identification system for relating items with patients and ensuring that an identified item corresponds to an identified patient. The patient identification system includes a computer system (42) interconnected to a plurality of remote terminals (62) by conventional telephone wiring (66,70). The patient identification system further including a portable bar code reading device (48) including a bar code wand (120), an LCD display (116) and a key pad (114). The portable bar code reading device (48) communicates via RF transmission with an RF/PLC modem (60). The bar code reading device (48) is utilized to read a patient's unique bar codes (50) on a patient's identification bracelet (52), bar codes (51) on labels (53) attached to various items in the hospital relating the item to a specific patient and bar codes (49) on item labels (47) whereby such items can be automatically correlated to a specific patient and checks performed at the computer system (42) to ensure that the item properly corresponds to the identified patient".

Additional background art includes U.S. Pat. Nos. 4,122,947, 3,848,112, 8,308,640 B2, and 4,476,381.

SUMMARY OF THE INVENTION

Some examples of some embodiments of the invention are listed below:

Example 1. A method for identity (ID) verification, comprising:
  acquiring one or more ID indications of at least one item using a handheld verifying device;
  automatically verifying by said verifying device a desired relation between the one or more acquired ID indications and at least one ID indication stored in a memory of the verifying device;
  physically marking said item using said verifying device with a verifying marking if said desired relation is automatically verified.

Example 2. A method according to example 1, comprising delivering of a positive human detectable indication by said verifying device if said desired relation is verified following said automatically verifying.

Example 3. A method according to any one of the previous examples, wherein said physically marking comprises physically marking said item with said ID verifying marking within a selected marking time window from said automatically verifying, wherein said selected marking time window is stored in said memory.

Example 4. A method according to any one of the previous examples, wherein said acquiring comprises acquiring said one or more ID indications within a selected acquiring time window from acquiring said stored ID indication, wherein said selected acquiring time window is stored in said memory.

Example 5. A method according to any one of the previous examples, comprises preventing said physically marking by said verifying device if said desired relation is not verified following said automatically verifying.

Example 6. A method according to any one of the previous examples, comprising storing an indication related to said automatically verifying and/or to said physically marking in said memory.

Example 7. A method according to example 6, comprising transmitting said indication by said verifying device to a remote device comprising one or more of a remote computer, a mobile device, a remote server, and/or cloud storage.

Example 8. A method according to any one of the previous examples, wherein said physically marking is allowed within a predetermined time period of up to 60 seconds from said automatically verifying.

Example 9. A verifying device, comprising:
  an identification (ID) reader configured to read one or more ID indications of at least one item;
  a memory configured for storing one or more ID indications;
  a control circuitry electrically connected to said ID indication reader and said memory configured for determining a relation between at least one ID indication read by said ID reader and said at least one stored ID indication;
  a marker functionally connected to said control circuitry configured for marking said item with a verifying marking, wherein said control circuitry allows said marker to mark said item with said verifying marking if said relation between said at least one read indication and said at least one stored indication is a desired relation.

Example 10. A verifying device according to example 9, comprising a user interface which delivers a human detectable indication if said desired relation is verified.

Example 11. A verifying device according to example 10, wherein said human detectable indication comprises an audio and/or or a visual indication.

Example 12. A verifying device according to any one of examples 9 to 11, comprising a marker lock functionally connected to the marker and to said control circuitry, wherein said marker lock is configured to prevent the activation of said marker.

Example 13. A verifying device according to example 12, wherein said control circuitry unlocks said marker lock to allow marking of said item with said verifying marking if said desired relation is verified.

Example 14. A verifying device according to any one of examples 12 or 13, wherein said marker lock comprises an electrical and/or a mechanical lock.

Example 15. A verifying device according to any one of examples 9 to 14, comprising a communication circuitry electrically connected to a control circuitry, wherein said communication circuitry is configured to transmit a signal to a remote device when said desired relation is verified.

Example 16. A verifying device according to example 15, wherein said remote device comprises a remote server or remote cloud storage.

Example 17. A verifying device according to any one of examples 15 or 16, wherein said remote device comprises a mobile device or a remote computer.

Example 18. A verifying device according to any one of examples 9 to 17, wherein said ID reader comprises an optical sensor configured to acquire an image of the one or more ID indications.

Example 19. A verifying device according to any one of examples 9 to 18, wherein said ID reader comprises a barcode reader or a 3D code reader.

Example 20. A verifying device according to any one of examples 9 to 19, wherein said marker comprises a stamp.

Example 21. A verifying device according to example 20, wherein said stamp comprises a self-inking stamp.

Example 22. A verifying device according to any one of examples 20 or 21, wherein said stamp comprises at least one marking head.

Example 23. A verifying device according to any one of examples 20 to 22, comprising an actuator configured to rotate said stamp.

Example 24. A verifying device according to any one of examples 9 to 23, wherein said device is shaped and size to be held by a single hand of an adult subject.

Example 25. A verifying device according to any one of examples 9 to 24, wherein a maximal length of said device is within a range of 5-17 cm.

Example 26. A verifying device according to any one of examples 9 to 25, wherein a maximal width of said device is within a range of 3-10 cm.

Example 27. A verifying device according to any one of examples 9 to 26, wherein a maximal weight of said device is within a range of 30-300 gr.

Example 28. A verifying device according to any one of examples 9 to 27, wherein said one or more read ID indications and said one or more stored ID indications are non-identical indications.

Example 29. A verifying device according to any one of examples 9 to 27, wherein said at least one item comprises a medical-related item.

Example 30. A verifying device according to example 29, wherein said medical-related item comprises one or more of a patient sample, a patient test result, a patient treatment, a patient location and/or patient-related documentation.

Example 31. A verifying device according to any one of examples 29 or 30, wherein said stored one or more ID indications and/or said one or more read ID indications comprise ID indications of a patient.

Some additional examples of some embodiments of the invention are listed below:

Example 1. A method for identity (ID) verification, comprising:

acquiring one or more ID indications of at least one item using a handheld verifying device; automatically verifying by said verifying device a desired relation between the one or more acquired ID indications and stored verification data associated with the verifying device; physically marking said item using said verifying device with a verifying marking if said desired relation is automatically verified.

Example 2. A method according to example 1, comprising delivering of a positive human detectable indication by said verifying device if said desired relation is verified following said automatically verifying.

Example 3. A method according to any one of the previous examples, wherein said physically marking comprises physically marking said item with said ID verifying marking within a selected marking time window from said automatically verifying, wherein said selected time window is stored in a memory associated with said verifying device.

Example 4. A method according to any one of the previous examples, wherein said acquiring comprises acquiring said one or more ID indications within a selected acquiring time window from acquiring said stored verification data, wherein said selected acquiring time window is stored in a memory associated with the verifying device.

Example 5. A method according to any one of the previous examples, comprises preventing said physically marking by said verifying device if said desired relation is not verified following said automatically verifying.

Example 6. A method according to any one of examples 1 to 4, comprising preventing said physically marking by said verifying device if a time window between a first automatically verifying and a second automatically verifying does not match said stored verification data.

Example 7. A method according to any one of the previous examples, comprising storing a verification indication related to said automatically verifying and/or to said physically marking in a memory.

Example 8. A method according to example 7, comprising transmitting said verification indication by said verifying device to a remote device comprising one or more of a remote computer, a mobile device, a remote server, and/or cloud storage.

Example 9. A method according to any one of the previous examples, wherein said physically marking is allowed within a predetermined time period of up to 60 seconds from said automatically verifying.

Example 10. A method according to any one of the previous examples, wherein said acquiring comprises acquiring one or more ID indications of at least one item associated with a drug manufacturing process, and wherein said automatically verifying comprises automatically verifying by said verifying device a desired relation between the one or more acquired ID indication and a stored protocol for manufacturing said drug associated with said verifying device.

Example 11. A method according to any one of examples 1 to 9, wherein said acquiring comprises acquiring one or more ID indication of at least one item associated with a cleaning or a sterilization procedure, and wherein said automatically verifying comprises automatically verifying by said verifying device a desired relation between the one or more acquired ID indication and a stored protocol for performing said cleaning or sterilization procedure associated with said verifying device.

Example 12. A method according to any one of examples 1 to 9, wherein said acquiring comprises acquiring one or more ID indications of at least one item associated with a set of medical tools and wherein said automatically verifying comprises automatically verifying by said verifying device a desired relation between the one or more acquired ID indication and a stored protocol for assembly of said medical tools set, associated with said verifying device.

Example 13. A verifying device, comprising:

an identification (ID) reader configured to read one or more ID indications of at least one item; a memory configured for storing one or more indications;
a control circuitry electrically connected to said ID indication reader and said memory configured for determining a relation between at least one ID indication read by said ID reader and said at least one stored indication;
a marking module functionally connected to said control circuitry configured for marking said item with a verifying marking, wherein said control circuitry allows said marking module to mark said item with said verifying marking if said relation between said at least one read indication and said at least one stored indication is a desired relation.

Example 14. A verifying device according to example 13, comprising a user interface which delivers a human detectable indication if said desired relation is verified.

Example 15. A verifying device according to example 14, wherein said human detectable indication comprises an audio and/or or a visual indication.

Example 16. A verifying device according to any one of examples 13 to 15, comprising a marking module lock functionally connected to the marking module and to said control circuitry, wherein said marking module lock is configured to prevent the activation of said marking module.

Example 17. A verifying device according to example 16, wherein said control circuitry unlocks said marking module lock to allow marking of said item with said verifying marking if said desired relation is verified.

Example 18. A verifying device according to any one of examples 16 or 17, wherein said marking module lock comprises an electrical and/or a mechanical lock.

Example 19. A verifying device according to any one of examples 13 to 18, comprising a communication circuitry electrically connected to a control circuitry, wherein said communication circuitry is configured to communicate with at least one remote device by transmitting and/or receiving wireless signals.

Example 20. A verifying device according to example 19, wherein said communication circuitry is configured to transmit a signal to said at least one remote device when said desired relation is verified.

Example 21. A verifying device according to any one of examples 19 or 20, wherein said at least one remote device comprises a remote server or a remote cloud storage.

Example 22. A verifying device according to any one of examples 19 to 21, wherein said at least one remote device comprises a mobile cellular device, a remote computer and/or a different ID verifying device.

Example 23. A verifying device according to any one of examples 19 to 22, wherein said control circuitry is configured to determine a relation between said at least one ID indication read by said ID reader and at least one indication stored in said at least one remote device by signaling said control circuitry to communicate with said at least one remote device.

Example 24. A verifying device according to example 23, wherein said at least one indication stored in said at least one remote device comprises at least one ID indication of a patient and/or at least one ID indication of a user of the ID verifying device.

Example 25. A verifying device according to any one of examples 19 to 24, wherein said communication circuitry is configured to receive a signal indicating a permission to use the verifying signal from said at least one remote device, and wherein said control circuitry allows said marking module to mark said item with said verifying marking if said permission indicating signal is received.

Example 26. A verifying device according to any one of examples 19 to 25, wherein said control circuitry signals said communication circuitry to transmit at least one of a log file, an ID indication read by said ID reader, information stored in said memory or indications thereof to said remote device.

Example 27. A verifying device according to any one of examples 13 to 26, wherein said ID reader comprises an optical sensor configured to acquire an image of the one or more ID indications.

Example 28. A verifying device according to any one of examples 13 to 27, wherein said ID reader comprises a barcode reader or a 3D code reader.

Example 29. A verifying device according to any one of c examples 13 to 28, wherein said marking module comprises a stamp.

Example 30. A verifying device according to example 29, wherein said stamp comprises a self-inking stamp.

Example 31. A verifying device according to any one of examples 29 or 30, wherein said stamp comprises at least one marking head.

Example 32. A verifying device according to any one of examples 29 to 31, comprising an actuator functionally connected to said control circuitry, configured to rotate said stamp.

Example 33. A verifying device according to any one of examples 13 to 32, wherein said device is shaped and size to be held by a single hand of an adult subject.

Example 34. A verifying device according to any one of examples 13 to 33, wherein a maximal length of said device is within a range of 5-17 cm.

Example 35. A verifying device according to any one of examples 13 to 34, wherein a maximal width of said device is within a range of 3-10 cm.

Example 36. A verifying device according to any one of examples 13 to 35, wherein a maximal weight of said device is within a range of 30-300 gr.

Example 37. A verifying device according to any one of examples 13 to 36, wherein said one or more read ID indications and said one or more stored indications are non-identical indications.

Example 38. A verifying device according to any one of examples 13 to 36, wherein said at least one item comprises a medical-related item.

Example 39. A verifying device according to example 38, wherein said medical-related item comprises one or more of a patient sample, a patient test result, a patient treatment, a patient location and/or patient-related documentation.

Example 40. A verifying device according to any one of examples 13 to 39, wherein said stored one or more ID indications and/or said one or more read ID indications comprise ID indications of a patient.

Example 41. A verifying device according to any one of examples 13 to 40, comprising a user ID verifying module electrically connected to said control circuitry, configured to read at least one biometric parameter of a user of the ID verifying device indicating user identity and/or permission of a user to use the ID verifying device.

Example 42. A verifying device according to example 41, wherein said user ID verifying module comprises a fingerprint reader, and wherein said at least one biometric parameter comprises a user fingerprint.

Example 43. A verifying device according to any one of examples 13 to 42, wherein said ID reader is configured to read at least one biometric parameter of a user of said verifying device and/or at least one biometric parameter of a patient.

Example 44. A verifying device, comprising:
an identification (ID) reader configured to read one or more ID indications of at least one item;
a communication circuitry configured to communicate with at least one remote device by transmitting and/or receiving wireless signals;
a control circuitry electrically connected to said ID indication reader and said communication circuitry, configured to determine a relation between at least one ID indication read by said ID reader and at least one indication stored in said remote device;
a marking module functionally connected to said control circuitry configured to mark said item with a verifying marking, wherein said control circuitry allows said marking module to mark said item with said verifying marking if said relation between said at least one read indication and said at least one stored indication is a desired relation.

Example 45. A device according to example 44, wherein said at least one remote device comprises a remote server or a remote cloud storage.

Example 46. A device according to any one of examples 44 or 45, wherein said at least one remote device comprises a mobile cellular device, a remote computer and/or a different ID verifying device.

Example 47. A device according to any one of examples 44 to 46, comprising a memory circuitry, wherein said control circuitry is configured to determine said relation between said at least one ID indication read by said ID reader and at least one indication stored in said memory circuitry.

Example 48. A verifying device according to any one of examples 44 to 47, wherein said ID reader comprises an optical sensor configured to acquire an image of the one or more ID indications.

Example 49. A verifying device according to any one of examples 44 to 48, wherein said ID reader comprises a barcode reader or a 3D code reader.

Example 50. A verifying device according to any one of examples 44 to 49, wherein said marking module comprises a stamp.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as identity verification, might be expected to use completely different methods, e g, making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A and 2B are block diagrams of devices for identity verification and marking, according to some exemplary embodiments of the invention;

FIG. 4 is a flow chart for a medical identity verification and marking process performed by a user, according to some exemplary embodiments of the invention;

FIGS. 7D-7G are schematic illustrations of an identity verifying stamp, according to some exemplary embodiments of the invention;

FIG. 9D is a flow chart of a process for a cleaning, for example sterilizing, procedure, according to some exemplary embodiments of the invention.

DESCRIPTION OF SPECIFIC EMBODIMENTS OF THE INVENTION

Figure 1:
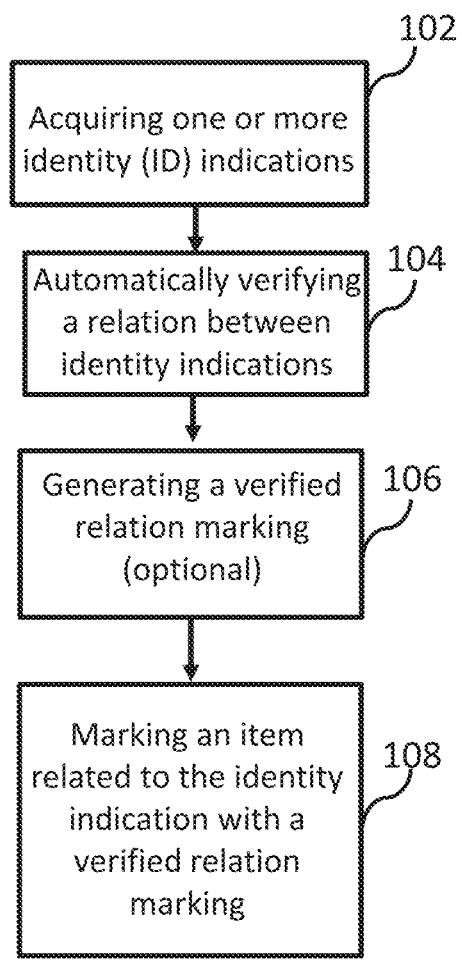
FIG. 1 is a flow chart of a general process for verifying one or more identity indications, according to some exemplary embodiments of the invention.

The present invention, in some embodiments thereof, relates to identity verification and, more particularly, but not exclusively, to identity verification of medical-related items.

A broad aspect of some embodiments of the invention relates to verifying marking of an item, for example by an ID marking. In some embodiments, the verification is performed by storing and/or transmitting an electronic verification signal to a memory circuitry, for example a memory circuitry of a verifying device, and/or a memory circuitry of a remote device. Alternatively or additionally, the verification is performed by adding an additional marking, for example a verification marking to the ID marking.

An aspect of some embodiments relates to verifying a desired relation between identities of two or more items, for example medical-related items. In some embodiments, at least one item of the two or more items is marked with a verified relation marking. In some embodiments, the verified relation marking is stamped on a surface, for example an outer surface, of the item. Alternatively or additionally, the verified relation marking is engraved, drawn or printed directly or indirectly on the surface of the medical-related item. In some embodiments, the verified relation marking is an electronical marking, for example an RFID marking which is delivered to a memory of the item. Optionally, the electronic marking is delivered to a memory of the medical-related item by wireless signals, for example by Bluetooth, Infra-red, and/or Wi-Fi signals.

According to some embodiments, a desired relation between a patient identity (ID) and an identity of a medical item is verified. In some embodiments, the medical item is marked with a visible verified relation marking and/or an electronically readable verified relation marking. A possible advantage of marking a medical idem with a verified relation marking is that it may allow rapid verification by a medical expert, for example a physician or a nurse, or a caregiver, that the medical item relates to a specific patient, and therefore to avoid mistakes due to wrong association between medical items and patients.

According to some embodiments, the relation between the patient ID and the medical item ID is verified when the patient or the patient ID and the medical item or the medical item ID are close to each other, for example in a distance of up to 10 meters from each other, up to 5 meters from each other, up to 3 meters from each other, up to 1 meter from each other or any intermediate, smaller or larger distance. Alternatively or additionally, the relation between the patient ID and the medical item ID is verified when the patient or the patient ID and the medical item or the medical item ID are both in the same field of view of a subject performing the verification. Alternatively or additionally, the relation between the patient ID and the medical item ID is verified when the patient or the patient ID, and the medical item or the medical item ID, are located at a distance of up to 3 meters, for example up to 2 meters, up to 1 meter or any intermediate, smaller or larger distance, from the eyes of a subject performing the verification.

According to some embodiments, the medical item comprises a storage compartment containing one or more medical samples extracted from a specific patient, for example blood samples, urine samples, stool samples, DNA samples, biopsy samples, tissue samples or any other medical samples. Additionally or alternatively, the medical item comprises one or more of drugs, blood infusion, food, patient accessories or storage compartments thereof. In some embodiments, a desired relation, for example a positive relation, between a patient ID and an ID of a storage compartment or an ID of a medical sample extracted from the patient located in the storage compartment is verified. In some embodiments, if the relation is a positive relation, then the storage compartment is marked with a verified relation marking.

According to some embodiments, the medical item comprises medical test results that are presented on a display, described in a document, for example a paper document and/or are stored in a memory storage media, for example a portable storage media. In some embodiments, the medical test results ID is presented on the display next to the presented results, on the document, and/or on a surface of the storage media, respectively. Optionally, the medical test results ID is stored in a memory storage of the storage media. In some embodiments, the medical test results comprise results of one or more of a blood test, a urine test, a stool test, a DNA test, a biopsy test, a tissue test, and/or any body tissue test. In some embodiments, the medical test results comprise results of a medical imaging technique, for example x-ray results, magnetic resonance imaging (MRI) results, computed tomography (CT) results, ultrasound results, mammogram results or any type of medical imaging results.

According to some embodiments, the medical item comprises a patient treatment. In some embodiments, a patient treatment ID is presented on a storage compartment of the patient treatment, for example on a storage compartment of a bio-active compound. Alternatively or additionally, the patient treatment ID is presented on a document, for example a paper document, associated with the storage compartment. In some embodiments, the patient treatment ID is stored in a memory circuitry of a storage compartment, for example a storage compartment of the bio-active compound.

According to some embodiments, an identity verification process of two identities, for example a patient ID and a medical item ID, is performed in a time delay between a verification process of a first pair of identities and following pairs of identities. In some embodiments, a time delay between consecutive verification processes is at least 30 seconds, for example 30 seconds, 60 seconds, 90 seconds, 120 seconds or any intermediate, smaller or larger time period. In some embodiments, reading a second ID, for example a medical item ID or a patient ID is performed within a selected time window of up to 15 seconds, for example up to 12 seconds or up to 8 seconds from reading a first ID.

According to some embodiments, at least one ID indication is acquired. In some embodiments, at least one ID indication is stored in a memory of a verifying device. In some embodiments, the at least one ID indication is acquired in a selected acquiring time window of up to 30 seconds, for example up to 20 seconds, up to 15 seconds, up to 10 seconds or any intermediate, smaller or larger time window from acquiring the at least one stored ID indication. In some embodiments, an item is marked, for example physically marked, within a selected marking time of up to 30 seconds, for example up to 20 seconds, up to 15 seconds, up to 10 seconds or any intermediate, smaller or larger time window from verifying a desired relation between two or more ID indications.

An additional potential advantage of the verifying device is that it may perform a reliable verification process at any location and by any user without the need to communicate with external devices during the verification process. This reliable verification process is important in order to reduce mistakes in systems when mistakes lead to enormous financial loss, for example in medical systems when it is crucial to reliably verify a relation between a patient and a medical item.

A potential advantage of marking an item with a visible verifying marking indicating a desired relation between two ID indications is that it may allow a person to quickly identify items with the visual verifying marking without the need of additional computers or communication systems.

An aspect of some embodiments relates to verifying activation of a marking module, for example a marker. In some embodiments, the marker comprises a stamp. In some embodiments, a verifying device comprising the marker receives an activation indication when the marker is activated. In some embodiments, the activation indication is stored in a memory of the verifying device. Alternatively or additionally, the activation indication is transmitted to a remote device, for example a remote mobile device, a remote server or cloud storage. In some embodiments, the activation indication comprises information regarding one or more of activation time, activation date, and/or activation location.

According to some embodiments, the activation indication is received from a feedback mechanism of the device. In some embodiments, the feedback mechanism comprises at least one sensor for sensing an activation of the marker, for example to sense when a stamp is placed in contact with a surface of an item.

An aspect of some embodiments relates to activating a marking module, for example a marker, according to results of a process verification procedure. In some embodiments, the marker is activated if at least one selected parameter of the process is verified. In some embodiments, the at least one selected parameter comprises a predetermined time window for completion of the process, a predetermined time window for performing a selected step of the process, number of process steps, order of process steps, a relation between the process and a subject, for example a patient and/or a subject authorized to perform the process.

According to some embodiments, a marker, for example a marker of an ID verifying device is activated if the at least one parameter of the process is verified. In some embodiments, a first marker of the ID verifying device is activated if the at least one process parameter is verified, and a different second marker is activated if the at least one process parameter is not verified. As used herein, activating a marker includes allowing activation of the marker, for example by deactivating a marker lock.

According to some embodiments, if the at least one process parameter is not verified, an alert signal is delivered to a user of the ID verifying device. Alternatively or additionally, if the at least one process parameter is not verified an alert signal is delivered to a remote device, for example a different ID verifying device, a remote computer, a cloud storage, and/or to a mobile device, for example a mobile cellular device.

According to some embodiments, the process to be verified comprises at least one of a process for manufacturing of bioactive components, for example medicines, drugs and/or cosmetic compounds, a process for preparation of surgical and/or medical tools, for example sets of surgical and/or medical tools, a process for preparation of a patient prior to a medical treatment, for example a surgical procedure, a process for cleaning and/or sterilizing equipment, for example medical equipment, and/or a process for preparation of food and/or delivery of food.

According to some embodiments, the process for manufacturing of bioactive compounds comprise, manufacturing of at least one of antibiotics, antibiotic solutions, chemotherapy medicines, psychotropic drugs, anti-viral drugs, and/or bioactive compounds personalized for a specific patient or a group of patients of up to 1000 patients, for example up to 100 patients, up to patients, up to 5 patients or any intermediate, smaller or larger number of patients.

According to some embodiments, the process for cleaning and/or sterilization comprise, sterilization of at least one medical device, sterilization or cleaning of an operating room, sterilization or cleaning of a trauma room, sterilization or cleaning of clothes, sterilization or cleaning of tools or equipment associated with a patient and/or with medical personnel, cleaning and/or sterilization of at least one room in a medical facility, for example a hospital or a clinic.

According to some embodiments, the process for assembly of a tool set comprise, a process for assembly of at least one surgical tool set, a process for assembly of medical kits, a process for assembly of tissue sampling and/or tissue analysis kits, a process for assembly of tool sets used in in-vitro fertilization processes, and/or a process for assembly of a tool set used in viral infectious subjects, for example HIV patients.

According to some embodiments, the ID verifying device is used to verify activation of at least one device, for example a machine, used in the process, for example a process for drug manufacturing, a cleaning and/or a sterilization process or a process for tool set assembly. In some embodiments, the activation of the machine is verified in order to make sure that the machine operates according to a desired protocol and/or within a desired range of operation parameter values. In some embodiments, the ID verifying device is used to verify the activation of the device by receiving information from the device, for example by wireless transmission and determining a relation between the received information and at least one stored indication, for example a verification indication.

According to some embodiments, the ID verifying device is used to verify activation of at least one machine used in preparation of drugs, for example a mixing machine, and/or an analysis machine. According to some embodiments, the ID verifying device is used to verify activation of at least one machine used in cleaning and/or sterilization, for example an autoclave, a sterilization device, and/or a washing machine.

According to some embodiments, the ID verifying device prevents the acquiring of a new ID indication or verification of a new ID indication, if a time window from acquiring of a previous ID indication does not match a desired time window, for example a desired time window stored in a memory of the ID verifying device or in a memory of a remote device or a cloud storage associated with the ID verifying device. In some embodiments, a desired time window is determined based on stored instructions or a stored protocol, for example a time window for performing at least one protocol step, a time window between two consecutive protocol steps or a time window in which a machine operates.

A potential advantage of using an ID verifying device to monitor and verify a process may be to make sure that a process is performed in a desired order of steps, in desired timing of each step and/or with desired components, and to provide a verification marking, for example a verification labeling accordingly. In some embodiments, the verification labeling is a quality assurance labeling, assuring that a process was performed and/or was completed according to desired requirements.

An aspect of some embodiments relates to activating a marking module, for example a marker of a verifying device, within one or more selected time windows. In some embodiments, the marker, for example a stamp, is allowed to be activated within a selected, optionally predetermined, activation time window. In some embodiments, an indication, for example a human detectable indication is delivered to a user of the marking device with information regarding the activation of the marker. In some embodiments, the indication is transmitted to a remote device, for example a remote computer, a mobile device, a remote server and/or cloud storage. Optionally, the positive indication is transmitted by a communication circuitry of the marker or the verifying device.

According to some embodiments, the ID verifying device is configured to communicate with a remote device, for example an application on a mobile or cellular device, a cloud storage, a remote server, and/or a remote computer. In some embodiments, the ID verifying device communicates with the remote device using a communication circuitry of the ID verifying device. In some embodiments, the ID verifying device communicates with the remote device, for example to authenticate an ID of a user of the device to make sure that the user is allowed to perform a specific action, for example a treatment or prescribe medications. Optionally, the ID verifying device authenticates an ID of the user by determining a relation between the user ID and/or permissions assigned to the user, with permissions assigned to the specific action. In some embodiments, if the determined relation between the user ID or permissions assigned to the user ID and at least one permission assigned to the specific action is not a desired relation, then the ID verifying device prevents the use of the marking module, for example the stamp.

According to some embodiments, the ID verifying device is configured to identify a specific user, for example to personalize a marking module, for example a stamp, to the specific user. In some embodiments, the ID verifying device identifies a user by measuring at least one biometric parameter, for example a user fingerprint or voice. In some embodiments, the ID verifying device comprises a user identification module configured to measure at least one parameter of the user, for example the biometric parameter. Optionally, the user identification module is the ID reader.

According to some exemplary embodiments, the user identification module comprises a fingerprint reader for reading the user fingerprint. Optionally, the ID reader of the ID verifying device comprises the fingerprint reader. In some embodiments, the user identification module, comprises an optic sensor, for example a camera, configured to acquire one or more visual parameters of a user of the ID verifying device. Optionally, when the user identification module is the ID reader, the ID reader is configured to acquire one or more visual parameters of a subject, for example a patient.

According to some embodiments, two or more ID authentications and/or permissions are required in order to allow marking, for example by allowing activation of a marking module or a stamp. In some embodiments, the ID verifying device is configured to receive two or more ID authentications and/or permissions by activating the ID reader and/or by communicating with a different device, for example a different ID verifying device, a remote server, a remote computer.

According to some embodiments, the ID verifying device comprises a memory, for example an internal memory. In some embodiments, the memory comprises a removable memory, for example a removable memory card or a removable memory circuit. In some embodiments, the memory stores ID information or indications thereof, at least one log file or any information related to the activity and/or function of the ID verifying device. In some embodiments, the ID verifying device is configured to allow reading of at least some information stored in the memory when the ID verifying device is in a specific activation mode, for example a maintenance mode. Alternatively or additionally, the ID verifying device is configured to allow reading of at least some information stored in the memory, when receiving at least one specific permission or when a specific user activates the ID verifying device.

Alternatively or additionally, at least some of the information acquired by the ID verifying device and/or log files related to the activity of the ID verifying device is stored in a memory external to the ID verifying device, for example in a remote server, in a remote computer, and/or in a cloud storage. In some embodiments, at least some of the information acquired by the device and/or at least some of the log files are encrypted. In some embodiments, permission to read information stored in the ID verifying device and/or in the remote device, is granted by a software stored in the ID verifying device or in the remote device.

According to some embodiments, a marking formed by a marking module, for example a marker, indicates and/or includes information regarding at least one deviation from a desired relation between at least one acquired ID indication and stored verification information and/or a stored protocol of a process. In some embodiments, the marking includes information regarding a modified protocol step and/or regarding a modified protocol component.

According to some embodiments, an ID verifying device is personalized for a specific user, for example by adjusting an activation protocol of the ID verifying device according to a user identity. In some embodiments, the ID verifying device acquires user identity using the ID reader and/or using one or more biometric modules, for example a fingerprint reader. In some embodiments, the ID verifying device generates different indications and/or delivers different information to different users, for example different indications and/or information will be delivered to medical personnel based on rank, training stage, seniority, and/or profession. For example, medical personnel in training will receive additional indications and/or information compared to indications and/or information presented to veteran or certified medical personnel.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary General Verification Process

According to some exemplary embodiments, a desired relation is verified between two or more acquired identity indications. In some embodiments, each of the identity indications is associated with an item, for example a medical-related item, a deliverable item or any physical or non-physical item. In some embodiments, at least one item associated with the verified identities is marked with a visible and/or an electronically readable verification marking, for example a verified relation marking. Reference is now made to FIG. 1 depicting a general process for verifying a relation between two identities and marking at least one item with a verification marking, according to some exemplary embodiments of the invention.

According to some exemplary embodiments, one or more identity (ID) indications are acquired at block 102. In some embodiments, two or more ID indications are acquired at block 102. In some embodiments, one or more of the acquired ID indications are stored in a memory, for example a memory of a device and/or cloud storage. In some embodiments, the one or more ID indications are acquired using a camera or a reader, for example a barcode reader, a QR code reader, an RFID reader or any other sensor configured to read a visible or an electronic signal.

According to some exemplary embodiments, a relation between the acquired ID indications is verified at block 104. In some embodiments, the relation between the acquired ID indications is automatically verified, for example by a verification device and/or by one or more algorithms stored in cloud storage. In some embodiments, a relation between one or more acquired ID indications and one or more stored ID indications is verified, for example automatically verified.

According to some exemplary embodiments, a relation between two or more ID indications is verified by comparing the two or more acquired ID indications and determining a relation between the compared ID indications. In some embodiments, determining a relation comprises determining if a relation between the two ID indications is a positive relation, for example a desired relation or a negative relation, for example an undesired relation between the ID indications.

According to some exemplary embodiments, a verification mark, for example a verified relation marking is generated at block 106. In some embodiments, the verified relation marking comprises a marking which is visible to an eye of a human subject or to an optical sensor, for example a camera. Alternatively the verified relation marking comprises an electronic marking which is readable by an electronic sensor, for example an RFID reader. In some embodiments, the verified relation marking includes information related to one or more of verification time, verification location, or verifying subject, for example an ID indication of the verifying subject. According to some exemplary embodiments, at least one item related to the acquired one or more ID indications, is marked at block 108 by a marking. In some embodiments, the at least one item is physically marked, for example by a stamp or a sticker. Alternatively, the at least one item is marked by an electronic label, for example a RFID label. In some embodiments, the electronic label is transmitted to the device by a wireless signal, for example a radio signal.

According to some exemplary embodiments, the marking is a visual marking which can be observed by a human subject. Alternatively or additionally, the marking is an electronically readable marking which can be read by an electronic sensor, for example an optic sensor or an RFID reader.

Exemplary Verification and Marking Device

According to some exemplary embodiments, a device for verifying a desired relation between a first ID indication and a second ID indication and for marking an item related to one or both of said first and second ID indications is a mobile device which is shaped and sized to be held by a user. In some embodiments, the device is small enough to be held and activated using a single hand of the user. In some embodiments, the device is small enough to be inserted into a pocket of a doctor coat or a lab coat. Alternatively, the device is attachable to the clothes or the body of a user. Reference is now made to FIG. 2A depicting a block diagram of a device for verifying a relation between two ID indications and for marking an item related to at least one item related to the two indications, according to some exemplary embodiments of the invention.

According to some exemplary embodiments, a device for verifying a desired relation between two ID indications and marking an item related to at least one of the ID indications, for example device 202 comprises a control circuitry 204, electrically connected to an ID reader, for example ID reader 206. In some embodiments, the ID reader is configured to read at least one ID indication, for example at least one ID indication associated with an item. In some embodiments, the item comprises a human subject, an animal, a patient, a medical-related item, a package for example a deliverable package or any other physical item.

According to some exemplary embodiments, the ID reader 206 comprises at least one optic sensor, for example a camera or a scanner. In some embodiments, the optic sensor is configured to read or acquire a code or an image, for example one or more of a 2D barcode, a 3D barcode, for example a QR code, a logo, or a graphical code. In some embodiments, the code or the image comprises an ID indication of a subject, for example a patient and/or an ID indication of an item, for example a medical-related item. In some embodiments, the ID indication is presented on a surface of the item, on patient-related documentation and/or on a display, for example a screen. In some embodiments, the optic sensor is configured to read a code visible to a naked eye of a human subject. Alternatively, the optic sensor is configured to read a code that is visible in selected wavelengths, for example after illuminating the code with light in specific wavelengths. In some embodiments, the device 202 comprises at least one light source 207, which emits visible light and/or light in selected wavelengths. In some embodiments, the at least one light source comprises an LED.

According to some exemplary embodiments, the ID reader comprises a radio frequency identification (RFID) reader configured to read RFID labels associated with at least one item. Alternatively or additionally, the ID reader comprises a Near Field Communication (NFC) reader which is configured to read information stored in one or more NFC tags associated with at least one item.

According to some exemplary embodiments, the control circuitry 204 signals the ID reader to read at least ID indication of an item and/or of a subject, for example a patient. In some embodiments, the read ID indication is stored in memory 208. In some embodiments, memory 208 stores ID indications, images of ID indications acquired by the optic sensor. Alternatively or additionally, the memory 208 stores at least one operation protocol of the device 202 or parameters thereof. In some embodiments, the memory 208 stores at least one database of ID indications, for example ID indications acquired by the ID reader 206. Alternatively or additionally, the memory 208 comprises at least one algorithm and/or at least one look up table for determining a relation between at least two acquired ID indications.

According to some exemplary embodiments, the device 202 comprises at least one user interface 210. In some embodiments, the user interface 210 comprises at least one button, for example a selection button and/or an activation button. Alternatively, the user interface 210 comprises at least one multi-purpose button for activation of the device and selection of activation protocols items or activation protocol functions. In some embodiments, the user interface 210 comprises at least one display. Alternatively or additionally, the user interface 210 comprises at least one speaker for generating audio indications and/or alerts, for example to a user of the device 202. Alternatively or additionally, the user interface 210 comprises at least one light source, for example an LED, for generating visual indications and/or alerts. In some embodiments, the user interface is used to generate alerts and/or or indications to a user of the device 202, for example to a physician, a nurse or any other medical personnel.

According to some exemplary embodiments, the device 202 comprises at least one communication circuitry 212 electrically connected to the control circuitry 204. In some embodiments, the communication circuitry comprises a transmitter, for example a wireless transmitter, configured to transmit wireless signals, for example Bluetooth signals, Wi-Fi signals, infra-red signals or any other wireless signal to one or more remote devices. In some embodiments, the remote device comprises a mobile device, for example a cellular device, a remote computer, a remote server, cloud storage or any other device which is not wirelessly connected to the device 202. Additionally or alternatively, the communication circuitry 212 comprises a receiver, for example a wireless receiver configured to receive wireless signals from the one or more of the remote devices.

According to some exemplary embodiments, the device 202 comprises a marking module, for example marker 214, electrically connected to the control circuitry 204. In some embodiments, the marker 214 is an integral part of the device 202. Alternatively, the marker comprises an external marker 216 functionally connected to the control circuitry 204 and/or to the communication circuitry 212. Optionally, the external marker is a removable or an add-on module to the device 202. In some embodiments, the marker is configured to physically mark an item, for example a medical-related item. In some embodiments, the marker is configured to mark a surface of the item, for example a document, a document attached to the item, a sticker attached to the item or any surface associated with the item. In some embodiments, the marker 214 is configured to mark an item with a visible marking, for example a marking which is visible to a naked eye of a human subject and/or to an optic sensor. In some embodiments, the marking comprises a 2D code, for example a barcode; a 3D code, for example a QR code; an image, a logo or any other visible graphical marking.

According to some exemplary embodiments, the marker 214 comprises a stamp, for example a mechanical and/or an electrical stamp. Alternatively or additionally, the marker 214 comprises a light marker, for example a laser making module, configured to engrave or generate a pattern having the shape of the marking on an item, for example on a surface of the item. Alternatively or additionally, the marker 214 comprises a printer, configured to print the marking directly on a surface, for example a surface of the item. In some embodiments, the printer comprises a sticker printer, configured to print one or more stickers with the marking. In some embodiments, the one or more stickers are shaped and sized to be attached to the item, for example to a surface of the item.

According to some exemplary embodiments, the marker 214 is configured to place two or more separate markings, for example a main marking and a secondary marking on an item. In some embodiments, the main marking comprises an ID marking, for example an ID marking of a subject, for example a user of the device. In some embodiments, the secondary marking comprises an ID verification marking, for example a marking which indicates that a desired relation between two or more ID indications is verified.

According to some exemplary embodiments, the marker 214 comprises two or more separate markers, for example a first marker and a second marker. In some embodiments, the first marker, for example a main marker is configured to place a main marking, for example an ID marking of a user of the device on an item. In some embodiments, the second marker, for example an auxiliary marker is configured to place a secondary marking, for example an ID verification marking on an item.

According to some exemplary embodiments, the device 202 comprises a feedback circuitry 213, electrically connected to the control circuitry 204. In some embodiments, the feedback circuitry is configured to deliver a feedback signal to the control circuitry 204 regarding the activation of the marker 214. In some embodiments, the feedback signal is delivered upon activation of the marker, for example when the marker marks an item. In some embodiments, the feedback signal is delivered by the feedback circuitry 2113 to the control circuitry if a marker 214 comprising a stamp is in contact with a surface of the item. In some embodiments, the feedback circuitry 213 comprises at least one sensor configured to sense an activation state of the marker, for example a contact sensor configured to sense a contact between the marker 214 and a surface of an item.

According to some exemplary embodiments, the device 202 comprises a lock, for example a marking module lock, also termed herein as a marker lock 216 electrically and/or mechanically connected to the marker, for example marker 214. In some embodiments, the lock moves between a locked state and an unlocked state. In some embodiments, the marker lock 216 moves between a locked state and an unlocked state according to signals received from the user interface 210. Alternatively or additionally, the marker lock 216 moves between the locked state and the unlocked state when a mechanical and/or a manual mechanism is activated by a user of the device 202. In some embodiments, the marker lock 216 is electrically connected to the control circuitry 204 which electrically control the activation of the marker lock 216. Alternatively, the marker lock 216 is mechanically operated. Optionally, the marker lock is manually operated.

According to some exemplary embodiments, when the marker lock 216 is in a locked state, the marker lock 216 prevents activation of the marker 214 for marking an item with the secondary marking. In some embodiments, when the marker lock 216 is in a locked state, the marker lock 216 prevents the activation of a second marker for marking an item with the secondary marking.

According to some exemplary embodiments, the device 202 comprises one or more orientation sensors 224, for example an accelerometer or a gyroscope. In some embodiments, the one or more orientation sensors 224 are configured to sense an orientation of the device 202 relatively to the ground or any other reference point. In some embodiments, as used herein, rotation of the device means roll, pitch and yaw of the device. Optionally, the one or more orientation sensors 224 are configured to sense an orientation of the ID reader 206 of the device 202 relative to the ground or any other reference point. In some embodiments, the one or more orientation sensors are configured to sense the orientation of the device 202 and/or the orientation of the ID reader 206 relative to a reference point in an X,Y,Z coordinate system. In some embodiments, the one or more orientation sensors provide information regarding the orientation of the device 202 and/or the ID reader 206 to the control circuitry 204 for example to ensure that the ID reader reads different ID indications and not the same ID indication twice.

According to some exemplary embodiments, the device 202 comprises at least one position sensor 225, electrically connected to the control circuitry 204. In some embodiments, the at least one position sensor 225 is configured to measure a position of the device in an X, Y, Z coordinate system. In some embodiments, the at least one position sensor comprises a global positioning system (GPS) sensor or any other position sensor that senses a position of the device 202.

According to some exemplary embodiments, the device 202 is a mobile device which is shaped and sized to be carried by a user, for example a physician. In some embodiments, the device 202 comprises a power source 220, for example an electrical power source. In some embodiments, the power source 220 is a rechargeable and/or a replaceable power source. In some embodiments, the power source 220 comprises at least one battery. In some embodiments, the power source 220 is electrically connected to a charging port 222 which is configured to be connected to an external electric charger.

According to some exemplary embodiments, the device 202 comprises a casing 226 which is shaped and sized to be handheld. In some embodiments, the device 202 has a maximal length in a range of 5-17 cm, for example 5-10 cm, 8-15 cm, 10-17 cm or any intermediate, smaller or larger range of values. In some embodiments, the device 202 has a maximal width in a range of 3-10 cm, for example in a range of 3-7 cm, 5-8 cm, 6-10 cm or any intermediate, smaller or larger range of values. In some embodiments, a maximal weight of the device 202 is in a range of 30-300 gr, for example 30-150 gr, 70-200 gr, 100-200 gr, 180-300 gr or any intermediate, smaller or larger range of values.

According to some exemplary embodiments, the device 202 comprises at least one optic sensor, for example a camera, configured to capture an image of a marking generated by the marker 214. In some embodiments, an activation indication of the marker comprises the captured image of the generated marking on the item. In some embodiments, the captured image of the marking is stored in the memory 208 of the device. In some embodiments, the stored captured image comprises a time and/or a date stamp, for example a stamp containing information related to the image capturing time and/or date. Additionally or alternatively, the stored captured image comprises a location stamp which includes coordinates or indications related to place in which the image was captured.

Figure 2B:
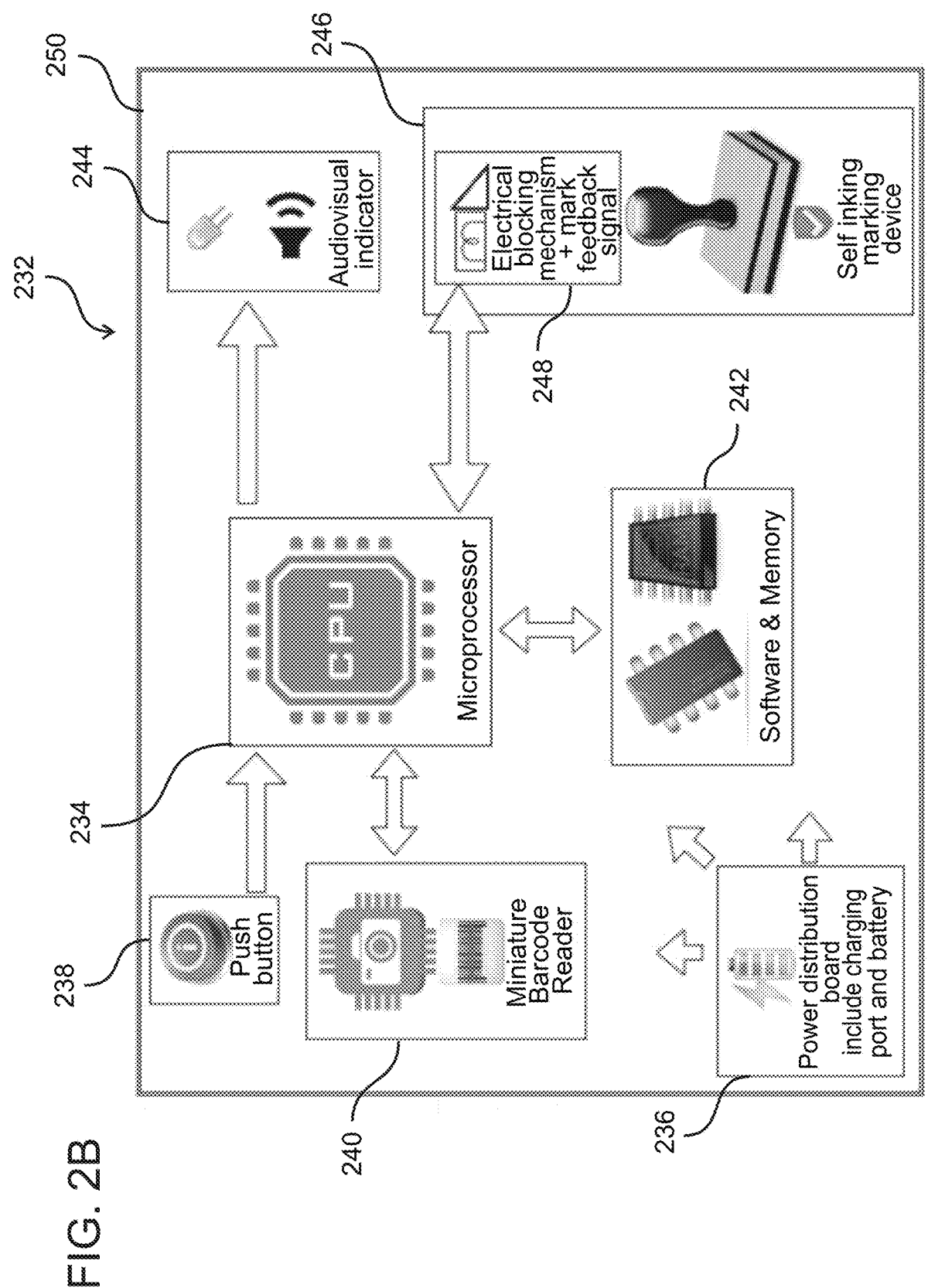

According to some exemplary embodiments, the device 202 comprises a timer 223, for example a timer circuitry or a timer module, electrically connected to the control circuitry 204. In some embodiments, the timer 223 is an integral module of the control circuitry 204. In some embodiments, the timer 223 is electrically connected to the marker lock 214, and is configured to set a time duration, for example an unlock time duration in which the marker lock is unlocked. In some embodiments, during the unlock time duration the marker 214 is active and can be used for marking an item. In some embodiments, when the time duration ends, the marker lock is automatically activated and locks the marker 214. In some embodiments, the unlock time duration is up to 120 seconds, for example up to 60 seconds, up to 30 seconds, up to 15 seconds, up to 10 seconds or any intermediate longer or shorter time period from activating the timer 223. Reference is now made to FIG. 2B depicting a verifying device which comprises a self-inking marking device, for example a stamp, according to some exemplary embodiments of the invention.

According to some exemplary embodiments, a verifying device, for example device 232 comprises a control circuitry, for example processor 234. In some embodiments, the processor 234 is electrically connected to a memory 242. In some embodiments, the memory 242 stores software, one or more algorithms, one or more look up tables and/or one or more ID indications. In some embodiments, the memory 242 comprises a removable memory which can be removed from the device 232.

According to some exemplary embodiments, the device 232 comprises at least one code reader, for example barcode reader 240. Optionally, the barcode reader comprises a miniature barcode reader. In some embodiments, the code reader is configured to read a 2D code, for example a barcode, and/or a 3D code, for example a QR code. In some embodiments, the code reader comprises an optic sensor, for example a camera, which is configured to acquire one or more images.

According to some exemplary embodiments, the device 232 comprises at least one user interface, for example a push button 238. In some embodiments, the push button 238 is a selection button. Alternatively or additionally, the push button 238 is an activation button. Optionally, the push button 238 is a multi-purpose button configured to be used for both activation and selection purposes. In some embodiments, the user interface comprises a display, for example to present one or more of activation options, selection menus, indications and alerts to a user of the device 232. In some embodiments, the push button 238 is used by a user of the device 232 to select an option from the selection menu presented on the display.

According to some exemplary embodiments, the device 232 comprises one or more indicators, for example an audiovisual indicator 244, electrically connected to the processor 234. In some embodiments, the one or more indicators are configured to deliver a human detectable indication, for example a visual and/or an audio indication to a user of the device 232. In some embodiments, a human detectable indication is delivered to the user when the verifying is ready for use, when reading a code by the code reader, for example barcode reader 240 and/or when a desired relation between two ID indications is verified.

According to some exemplary embodiments, the device 232 comprises one or more markers, for example a stamp 246, electrically connected to the processor 234. In some embodiments, the marker is configured to mark an item with a marking, for example a verifying marking. In some embodiments, the marker, for example the stamp 246 comprises a locking module, for example a lock 248. In some embodiments, the lock is configured to prevent the activation of the marking device, for example the stamp 246, for example when a desired relation between two ID indications is not verified by the processor 234.

According to some exemplary embodiments, the device 232 comprises at least one marking feedback sensor, for example as part of the lock 248. In some embodiments, the marking feedback sensor is configured to sense the activation of the stamp 246, and to deliver a feedback signal to the processor 234. In some embodiments, the at least one marking feedback sensor comprises a mechanical contact sensor, ultrasonic sensor, optical sensor, capacitive sensor or induction sensor.

According to some exemplary embodiments, the device 232 is a mobile device, and comprises a power source 236, for example a rechargeable power source. In some embodiments, the power source 236 comprises a power distribution circuitry and/or a battery. Optionally, the battery comprises a replaceable battery.

Exemplary Verifying Process

Figure 3A:
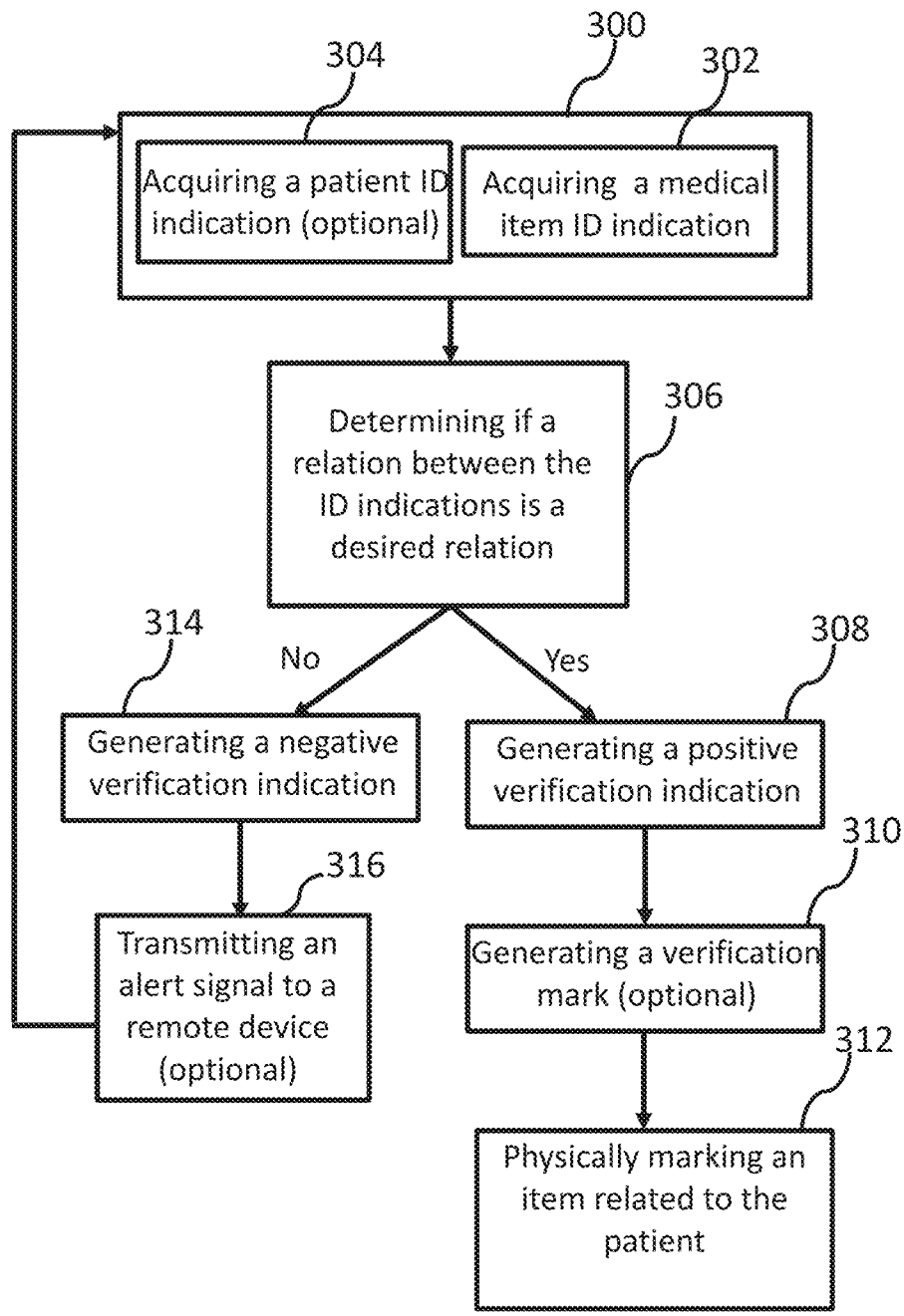
FIGS. 3A, 3B and 3C are flow charts of an ID verification process performed by a verifying device, according to some exemplary embodiments of the invention.

According to some exemplary embodiments, the verifying device, for example verifying device 202 or 232 verifies a desired relation between two or more ID indications. Reference is now made to FIG. 3A depicting a verifying process performed by a verifying device, according to some exemplary embodiments of the invention.

According to some exemplary embodiments, the verifying device, for example device 202 or device 232 shown in FIGS. 2A and 2B respectively, acquires, for example by reading, one or more ID indications at block 300. In some embodiments, the verifying device reads a first indication, for example a medical item ID indication at block 302. Additionally, the verifying device reads a second indication, for example a patient ID indication at block 304. In some embodiments, the device 202 reads the one or more ID indications by ID reader 206 and stores the read indications in memory 208. In some embodiments, the device 232 reads the one or more ID indications by code reader 240, and stores the read indications in memory 242.

According to some exemplary embodiments, the verifying device determines if a relation between the acquired ID indications is a desired relation at block 306. In some embodiments, the control circuitry 204 of device 202 determines if a desired relation between the two acquired ID indications is a desired relation using at least one ID indication and/or at least one algorithm or look up table stored in memory 208. In some embodiments, the processor 234 of device 232 determines if a desired relation between the two acquired ID indications is a desired relation using at least one ID indication and/or at least one algorithm or a look up table stored in memory 242. Alternatively or additionally, the device determines whether a relation between the two acquired ID indications using one or more algorithms and/or a look up table stored in a remote server or a remote cloud storage.

According to some exemplary embodiments, if a relation between the two or more acquired ID indications is not a desired relation, a negative verification indication, for example a verification alert signal, is generated at block 314. Additionally, the generated negative verification indication is delivered to a user of the device at block 314. In some embodiments, the negative verification signal is generated by user interface 210 of device 202 or by indicator 244 of the device 232.

According to some exemplary embodiments, the negative verification indication, for example an alert signal, is transmitted to a remote device at block 316. In some embodiments, the remote device comprises one or more of a remote mobile device, a remote computer, a remote server and/or remote cloud storage. In some embodiments, the negative verification indication is transmitted to the remote device using a communication circuitry of the device, for example communication circuitry 212 of the device 202.

According to some exemplary embodiments, if a relation between the two or more acquired ID indications is a desired indication, a positive verification indication is generated at block 308. Additionally, the positive verification indication is delivered to a user of the device at block 308. In some embodiments, the positive verification indication is generated by user interface 210 of device 202 or by indicator 244 of the device 232. In some embodiments, the positive verification indication is transmitted to a remote device, for example as described at block 316, using a communication circuitry of the device, for example communication circuitry 212 of the device 202.

According to some exemplary embodiments, a verification mark is generated at block 310. In some embodiments, the verification mark is generated to include information or data indicating a positive verification of the desired relation between the two or more acquired ID indications. Alternatively, the verification mark is a fixed verification mark that is not changed between different verification sessions.

According to some exemplary embodiments, the verifying device physically marks an item, for example an item related to the patient or to one or more of the acquired indications, at block 312. In some embodiments, the verifying device marks the item with a verification mark, for example the generated verification mark or a fixed verification mark, for example a predetermined verification mark. In some embodiments, the verifying device, for example device 202 or device 232 marks the item using the marker 214 or stamp 246, respectively. In some embodiments, when the desired relation between the acquired ID indications is verified, a marker lock, for example lock 216 of device 202 or lock 248 of device 232 is unlocked, for example to allow the physically marking of the item.

Figure 3B:
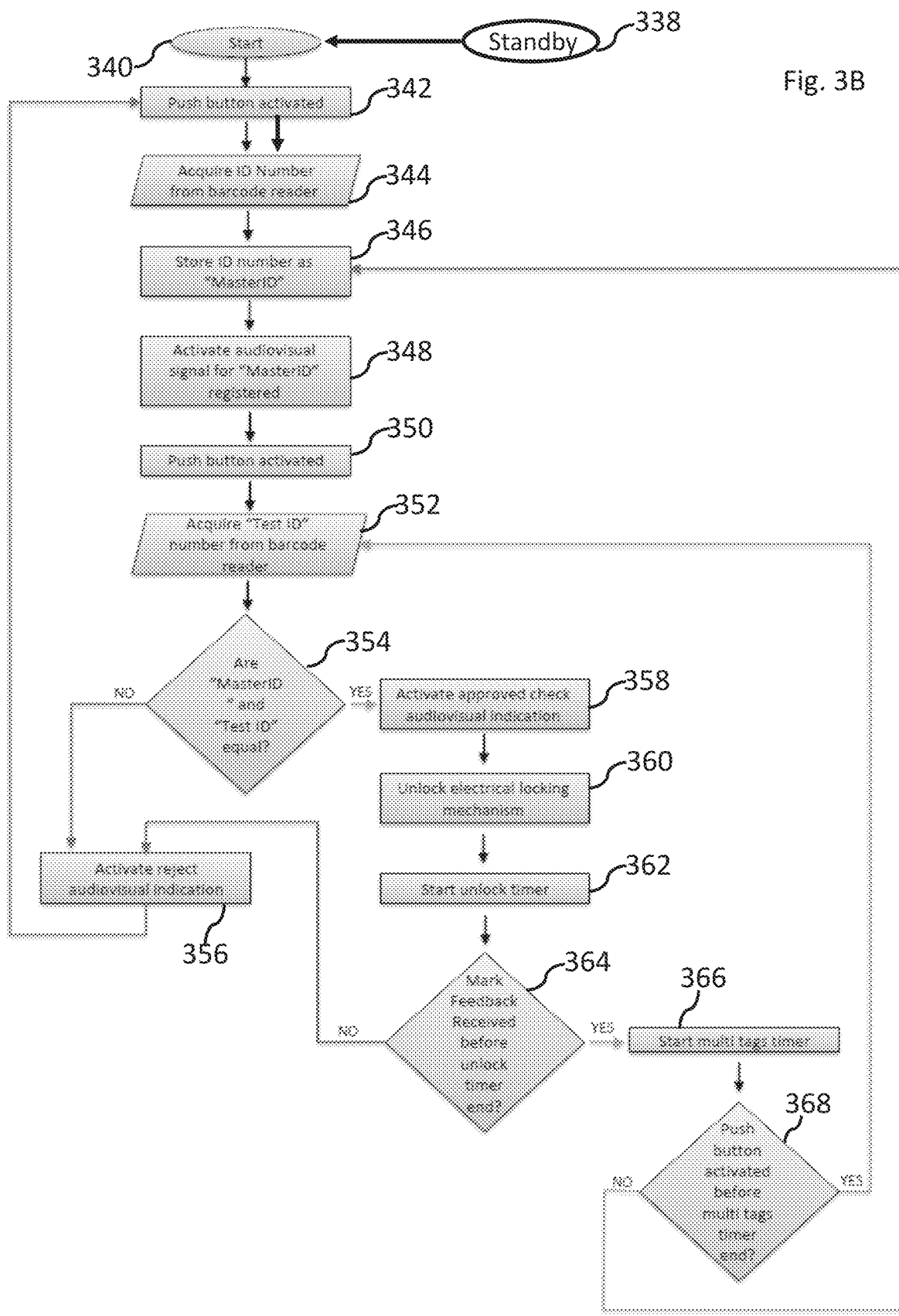

Reference is now made to FIG. 3B depicting a verifying and stamping process, for example using the device 232 shown in FIG. 2B, according to some exemplary embodiments of the invention.

According to some exemplary embodiments, a verifying device, is at a standby mode at block 338. In some embodiments, the verifying device is used as a marking device, for example as a stamp without initiating a verification process.

According to some exemplary embodiments, a verifying process initiates at block 340. In some embodiments, the verifying process is initiated by receiving a signal from a user of the device, for example from a user interface of the device. Alternatively or additionally, the verifying device shifts from a standby mode to an operating mode when receiving signals from one or more orientation sensors, for example when the device is tilted, rotated, moved or elevated from a surface. In some embodiments, the verifying process is initiated by activating a push button at block 342. Alternatively or additionally, the verifying process is initiated by receiving a signal from one or more orientation sensors of the device, for example orientation sensors 224 shown in FIG. 2A. In some embodiments, the signal from the orientation sensors is received when moving the device in a specific direction, for example when rotating the device.

According to some exemplary embodiments, a first ID indication is acquired at block 344. In some embodiments, the ID indication, for example an ID number, is acquired using the ID reader 206 shown in FIG. 2A, or the code reader 240 shown in FIG. 2B.

According to some exemplary embodiments, the first acquired ID indication is stored in a memory of the device, for example memory 208 of the device 202 or memory 242 of the device 232, at block 346. In some embodiments, the first acquired ID indication is registered as a Master ID.

According to some exemplary embodiments, an indication, for example a human detectable indication, is generated at block 348. In some embodiments, the indication is generated following the acquiring, storing, and/or registering the first acquired ID indication, for example the registered Master ID.

According to some exemplary embodiments, the user interface delivers a signal prior to acquiring a second ID indication at block 350. In some embodiments, a push button is activated at block 350, prior to acquiring the second ID indication.

According to some exemplary embodiments, a second ID indication is acquired at block 352. Optionally, in order to acquire the second ID indication, a signal from the user interface must be received or the push button must be activated. In some embodiments, the second ID indication is acquired using the code reader 240 or the ID reader 206.

According to some exemplary embodiments, the second ID indication is acquired at predetermined time duration of up to 30 seconds, for example up to 20 seconds, up to 15 seconds or any intermediate, shorter or longer time duration from the acquiring of the first ID indication. In some embodiments, if the second ID indication is not acquired within the predetermined time duration, then an alert signal is delivered to a user. Additionally or alternatively, the user must repeat the acquiring of the first ID indication at block 344.

According to some exemplary embodiments, the second acquired ID indication is stored in a memory of the device. In some embodiments, the second ID indication is registered as Test ID.

According to some exemplary embodiments, a control circuitry, for example a processor of the device determines whether a relation between the Master ID and the Test ID is a desired relation at block 354. In some embodiments, a desired relation comprises a desired similarity between the Master ID and the Test ID. In some embodiments, the desired similarity comprises complete similarity between the Master ID and the Test ID. In some embodiments, the control circuitry determines if the relation is a desired relation using at least one algorithm and/or at least one look up table stored in a memory circuitry of the device. Alternatively or additionally, the control circuitry determines if the relation is a desired relation using at least one algorithm and/or at least one look up table stored in a remote server or cloud storage.

According to some exemplary embodiments, if the determined relation is not a desired relation, then a negative indication is generated, for example an alert signal, at block 356. In some embodiments, the negative indication is generated using a user interface, for example the user interface 210, or the audio visual indicator 244. In some embodiments, the negative indication comprises a negative audiovisual indication, for example a reject audiovisual indication. In some embodiments, if the determined relation is not a desired relation, then an indication, for example a negative indication, is transmitted to a remote device, for example a remote computer, a remote server or remote cloud storage. Alternatively or additionally, the negative indication is stored in a memory of the device.

According to some exemplary embodiments, if the determined relation is a desired relation, then a positive indication is generated at block 358. In some embodiments, the positive indication comprises an audio and/or a visual indication, for example a human detectable indication. In some embodiments, the positive indication is generated using a user interface, for example the user interface 210, or the audio visual indicator 244. In some embodiments, if the determined relation is a desired relation, then an indication, for example a positive indication, is transmitted to a remote device, for example a remote computer, a remote server or remote cloud storage. Alternatively or additionally, the positive indication is stored in a memory of the device.

According to some exemplary embodiments, if the determined relation is a desired relation, then a locking mechanism is unlocked at block 360. In some embodiments, when the locking mechanism is in a locked state, the locking mechanism prevents the activation of a marker of the device. Alternatively when the locking mechanism is in a locked state, the locking mechanism prevents activation of a verification marker while allowing the activation of an ID marker. In some embodiments, when the locking mechanism is in an unlocked state, the verifying marker can be activated to generate a verification marking. In some embodiments, the locking mechanism comprises an electrical lock, electrically connected to the control circuitry, for example a processor of the device.

According to some exemplary embodiments, an unlock timer is initiated at block 362. In some embodiments, the unlock timer relates to a maximal predetermined time duration for activating a marker. In some embodiments, the predetermined time duration comprises a time duration of up to 30 seconds, for example up to 20 seconds, up to 15 seconds, up to 10 seconds or any intermediate, shorter or longer time duration following unlocking of the marker and/or determining that a relation is a desired relation.

According to some exemplary embodiments, the device determines whether a marking feedback is received prior to unlock timer ends at block 364. In some embodiments, the marking feedback is received from at least one sensor, for example a pressure sensor or a contact sensor located at or near the marker.

According to some exemplary embodiments, if the feedback is not received during the predetermined time duration of the timer activation or is received after the timer activation has ended, then a negative indication is generated at block 356.

According to some exemplary embodiments, if a marking feedback is received during the predetermined timer activation period, then a multi-tags timer is activated at block 366. In some embodiments, activation of the multi-tags timer allows to set a time period in which additional Test ID indications are acquired, for example when multiple items are related to a single Master ID-related item.

According to some exemplary embodiments, the device determines if a signal is received from a user interface, for example if a push button is activated, during the activation time period of the multi-tags timer, at block 368. In some embodiments, if a signal is not received from the user interface during the predetermined activation time period of the multi tags timer, then the device return to a standby mode at block 338. According to some exemplary embodiments, if a signal is received during the activation time period of the multi tags timer, then an additional single Test ID is acquired at block 352.

Figure 3C:
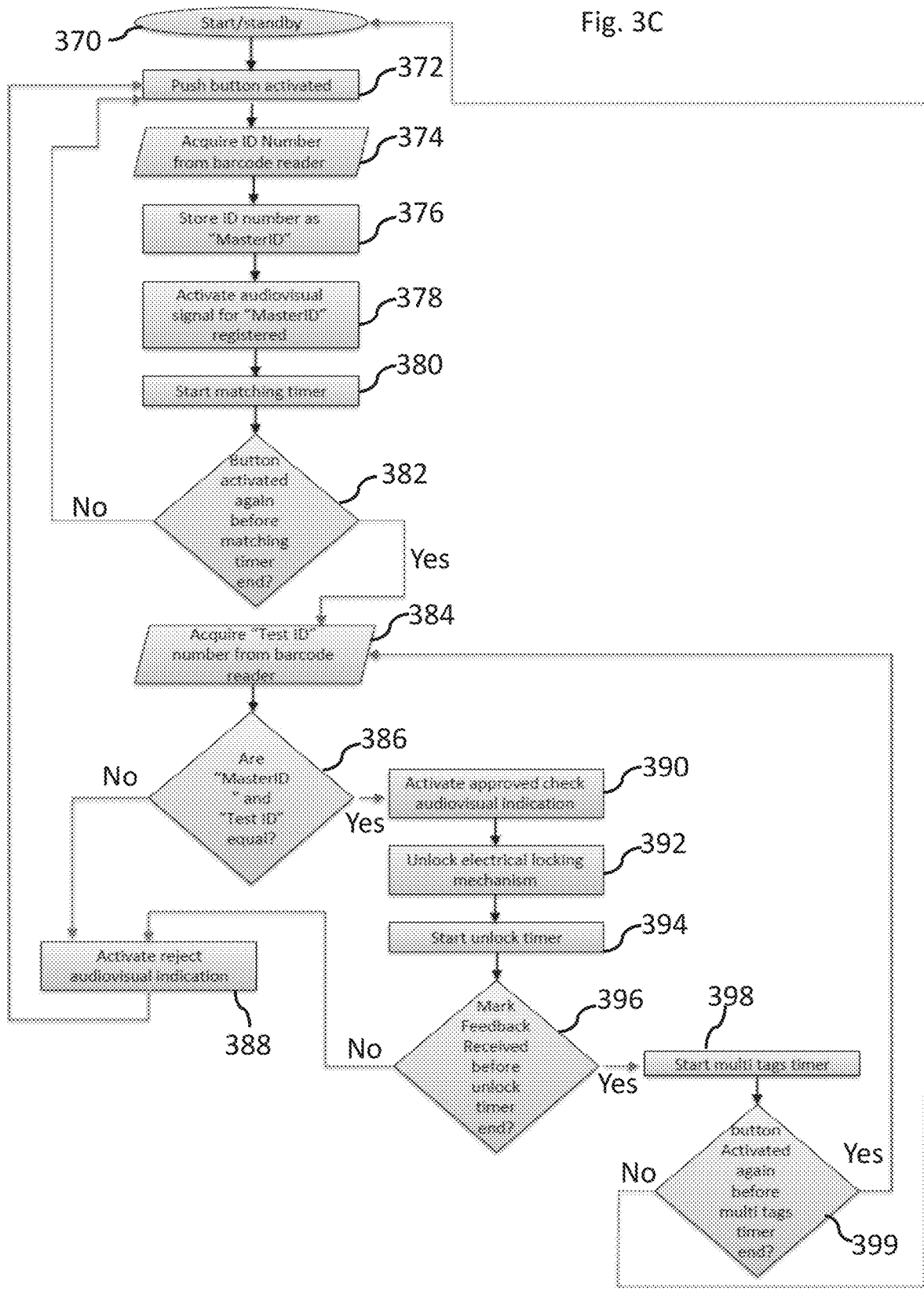

Reference is now made to FIG. 3C depicting a verifying and stamping process, for example using the device 232 shown in FIG. 2B, according to some exemplary embodiments of the invention.

According to some exemplary embodiments, a verifying device, is at a standby mode at block 370. In some embodiments, for example when the device is in a standby mode, the verifying device is used as a marking device, for example as a stamp without initiating a verification process. In some embodiments, the verifying process is initiated by receiving a signal from a user of the device, for example from a user interface of the device. Alternatively or additionally, the verifying device shifts from a standby mode to a start mode at block 370 when receiving signals from one or more orientation sensors, for example when the device is tilted, rotated, moved or elevated from a surface.

According to some exemplary embodiments, a signal is received from a user at block 372. In some embodiments, the signal is received via a user interface of the device. Optionally, the user is received when a button, for example a push button, is activated at block 372. In some embodiments, the button is activated in order to activate a reader of the device, for example the ID reader 206 of the device 202 shown in FIG. 2A or code reader 240 of the device 232 shown in FIG. 2B.

According to some exemplary embodiments, an ID indication, for example a first ID indication is acquired, at block 374. In some embodiments, the ID indication is acquired by activating the reader of the device. Alternatively or additionally, the ID indication is acquired by placing a tag of an item containing the ID indication in the field of view of the device reader. In some embodiments, the ID indication is acquired at block 374 by placing a tag of an item containing the ID indication sufficiently close, for example at a distance of up to 10 meters, for example up to 5 meters, up to 3 meters, up to 1 meters, up to 0.5 meters or any intermediate, smaller or larger distance from the reader of the device.

According to some exemplary embodiments, the first read ID indication is stored in a memory of the device at block 376. In some embodiments, the first ID indication is registered or is stored in the memory as a MasterID.

According to some exemplary embodiments, the user interface transmits an indication, for example an audio and/or a visual indication at block 378. In some embodiments, the user interface transmits the indication to indicate a reading of an ID and/or the registering of an ID in the memory.

According to some exemplary embodiments, a timer is activated at block 380. In some embodiments, the timer comprises a matching timer which defines a matching time window between the acquiring of a first ID indication and the acquiring of a second ID indication. Alternatively, the matching timer defines a time window between the acquiring or registering of the first ID indication and determining a relation between the first ID indication and a second ID indication. In some embodiments, the timer sets a matching time duration of up to 30 seconds, for example up to 20 seconds, up to 15 seconds, up to 10 seconds or any intermediate, shorter or longer time duration from reading the first ID indication.

According to some exemplary embodiments, the device determines whether a signal has received from the user interface, for example if a button is activated within the matching time, at block 382. In some embodiments, if a signal is not received within the matching time duration, then the device returns to a standby state at block 370. Alternatively, if the signal was not received within the matching time duration, then the device waits for the reading a first ID indication at block 374. In some embodiments, if the signal was not received within the matching time duration, then the device waits to receive a signal from the user interface at block 372 prior to the reading of the first ID indication in block 374. In some embodiments, if the signal was not received within the matching time duration, then the previously stored ID indication, that optionally was stored as a MasterID, is erased from the memory of the device or is archived.

According to some exemplary embodiments, the timer sets a matching time duration of up to 30 seconds, for example up to 20 seconds, up to 15 seconds, up to 10 seconds or any intermediate, shorter or longer time duration from reading the first ID indication and reading a second ID indication. In some embodiments, if the device does not read a second ID indication within the matching time duration then the device returns to a standby state.

According to some exemplary embodiments, if a signal is received from the user interface within the matching time duration, then a second ID indication is acquired at block 384. In some embodiments, the second ID indication is acquired as described, for example, in block 374. In some embodiments, the acquired second ID indication is stored in a memory of the device. In some embodiments, the second ID indication is stored or is registered in the memory of the device as TestID.

According to some exemplary embodiments, a relation is determined between the first acquired ID indication, for example the stored MasterID, and the second acquired ID indication, for example the TestID, at block 386. In some embodiments, a desired relation between the first acquired ID indication and the second acquired ID indication is verified at block 386. In some embodiments, the desired relation is defined as a relation in which the first acquired ID indication is identical to the second acquired ID indication. Alternatively, the desired relation is defined as a relation in which the two acquired ID indications are not identical, but have a predetermined relation between them. In some embodiments, a predetermined relation between the two non-identical ID indications comprises a relation via an algorithm, stored for example in a memory of the device. Alternatively or additionally, a predetermine relation between the two non-identical ID indications comprise a predetermined relation of the two ID indications to one or more indications, for example one or more indications stored in the memory of the device.

According to some exemplary embodiments, if a desired relation between the two acquired ID indications is not verified at block 386, then a negative indication is generated and optionally delivered to a user of the device, at block 388. In some embodiments, the negative indication comprises a human detectable negative indication, for example an alert signal. In some embodiments, the alert signal comprises an audio and/or a visual alert signal.

According to some exemplary embodiments, if a desired relation between the two acquired ID indications is verified at block 386, then a positive indication is generated, and optionally delivered to a user of the device at block 390. In some embodiments, the positive indication comprises a human detectable indication, for example an audio and/or a visual indication.

According to some exemplary embodiments, if a desired relation between the two acquired ID indications is verified, then a marker locking mechanism, for example a marker lock is unlocked or deactivated at block 392. In some embodiments, the marker lock, for example marker lock 216 shown in FIG. 2A or lock 248 shown in FIG. 2B, comprises a mechanical and/or an electrical lock.

According to some exemplary embodiments, an unlock timer is initiated at block 394. In some embodiments, the unlock timer sets an unlock time period, for example a time period in which the marker remains unlocked. In some embodiments, the unlock time period is up to 60 seconds, up to 30 seconds, up to 20 seconds, up to 10 seconds or any intermediate, shorter or longer time period from determining at block 386 that a relation is a desired relation, or from the transmitting of a positive indication at block 390 or from the unlocking of the marker lock at block 392.

According to some exemplary embodiments, the device determines whether a marker is activated within the unlock time period at block 396, for example by receiving a marking feedback signal. In some embodiments, the marking feedback signal is received from the marker and/or from one or more sensors of the device. In some embodiments, if a marking signal is not received during the unlock time period, then a negative indication if generated and optionally transmitted to the user of the device at block 388.

According to some exemplary embodiments, the marker is activated during the unlock time period. Optionally, the marker is activated only during the unlock time period. In some embodiments, the marker is locked automatically when the unlock time period ends. Alternatively, the marker is locked automatically after receiving a marking feedback signal. In some embodiments, the marker lock and/or the unlock timer allow a single marking when the marker is unlocked.

According to some exemplary embodiments, a multi tags timer is initiated at block 398. In some embodiments, the multi tags timer sets a multi tags time duration in which two or more markings are performed, for example 2, 3, 4, 5 or any larger number of marking is performed based on a single verification of a desired relation. Alternatively or additionally, the multi tags timer sets a multi tags time duration in which two or more TestID's are acquired, and a relation determination between each of the two or more test ID's to a single MasterID is performed. In some embodiments, the multi tags time duration is up to 60 seconds, for example up to 30 seconds, up to 20 seconds or any intermediate, shorter or longer time duration from receiving a feedback at block 396.

A potential advantage of acquiring multiple TestID indications and comparing them to a single MasterID indication one after another, is that it allows to save time in situations in which several TestID indications, for example indications of several tissue sample tubes, exist for the same patient having a single ID indication, for example a MasterID indication.

According to some exemplary embodiments, the device determines whether a signal is received from a user interface of the device, for example if a button is activated, during the multi tags time duration at block 399. In some embodiments, if a signal is received from the user interface during the multi tags time duration, then an additional ID indication, for example an additional TestID is acquired, for example as described at block 384.

According to some exemplary embodiments, if a signal from the user interface is not received during the multi tags time duration, then the device returns to a standby state at block 370.

Exemplary User Activation of a Verifying Device

According to some exemplary embodiments, a user of the verifying device is carrying the verifying device with him. In some embodiments, the verifying device is used as a marking device, for example a stamp, without verifying a relation between two identities. In some embodiments, a verifying mode of the device is activated when receiving a signal from a user, for example via a user interface of the verifying device. Alternatively or additionally, the verifying mode of the device is activated when receiving a signal from at least one sensor of the device, for example an orientation sensor of the device that senses when the device is tilted, moved, rotated or is lifted from a surface. Reference is now made to FIG. 4, depicting an activation of a verifying process by a user of the verifying device, according to some exemplary embodiments of the invention.

According to some exemplary embodiments, once a verification process is initiated, a user reads a first ID indication, for example an ID indication of a patient at block 402. In some embodiments, in order to read an ID indication, the user needs to activate the ID reader, for example a barcode reader or a camera of the device. In some embodiments, the user activates the ID reader by interacting with a user interface of the device, for example the user interface 210 of the device 202 shown in FIG. 2A or a push button 238 of the device 232 shown in FIG. 2B.

According to some exemplary embodiments, a user reads a second ID indication, for example a medical item ID indication at block 404. In some embodiments, the user reads the second ID indication within a predetermined time duration from reading the first ID indication. In some embodiments, the time duration comprises a time duration of up to 30 seconds, for example up to 15 seconds, up to 10 seconds or any intermediate, shorter or longer time period from reading the first ID indication. In some embodiments, if the user fails in reading the second ID indication within the predetermined time duration, then the user receives a negative feedback, for example an alert signal.

According to some exemplary embodiments, the user receives a negative human detectable indication, for example an alert signal, at block 410, if a relation between the two read ID indications is not a desired relation. Alternatively, the user receives a positive human detectable indication at block 406, if a relation between the two read ID indications is a desired relation. In some embodiments, both the negative and the positive human detectable indications comprise at least one audio and/or visual indication.

According to some exemplary embodiments, the user marks an item related to one or more of the ID indications with a verification marking at block 408. In some embodiments, the user physically marks the item. Alternatively, the user virtually marks the item, for example by transmitting a verification signal to a memory of the item. In some embodiments, the verification signal is stored in a memory of the item and can be read by a reader, for example a RFID reader.

According to some exemplary embodiments, the user marks the item within a predetermined time duration, for example a marking time duration from receiving the positive indication at block 406. In some embodiments, the user needs to complete the marking process within the predetermined time duration. In some embodiments, the time duration comprises a time duration of up to 30 seconds from receiving the positive indication at block 406, for example a time duration of up to 20 seconds, up to 15 seconds, up to 10 seconds or any intermediate, shorter or longer time duration from receiving the positive indication.

According to some exemplary embodiments, marking is not performed within the predetermined time period then the user receives an alert signal. Additionally, in some embodiments, the user must start the verification process from the beginning, and read the first ID indication again.

Exemplary Verifying Device Interactions with Items in a Medical Environment

Figure 5:
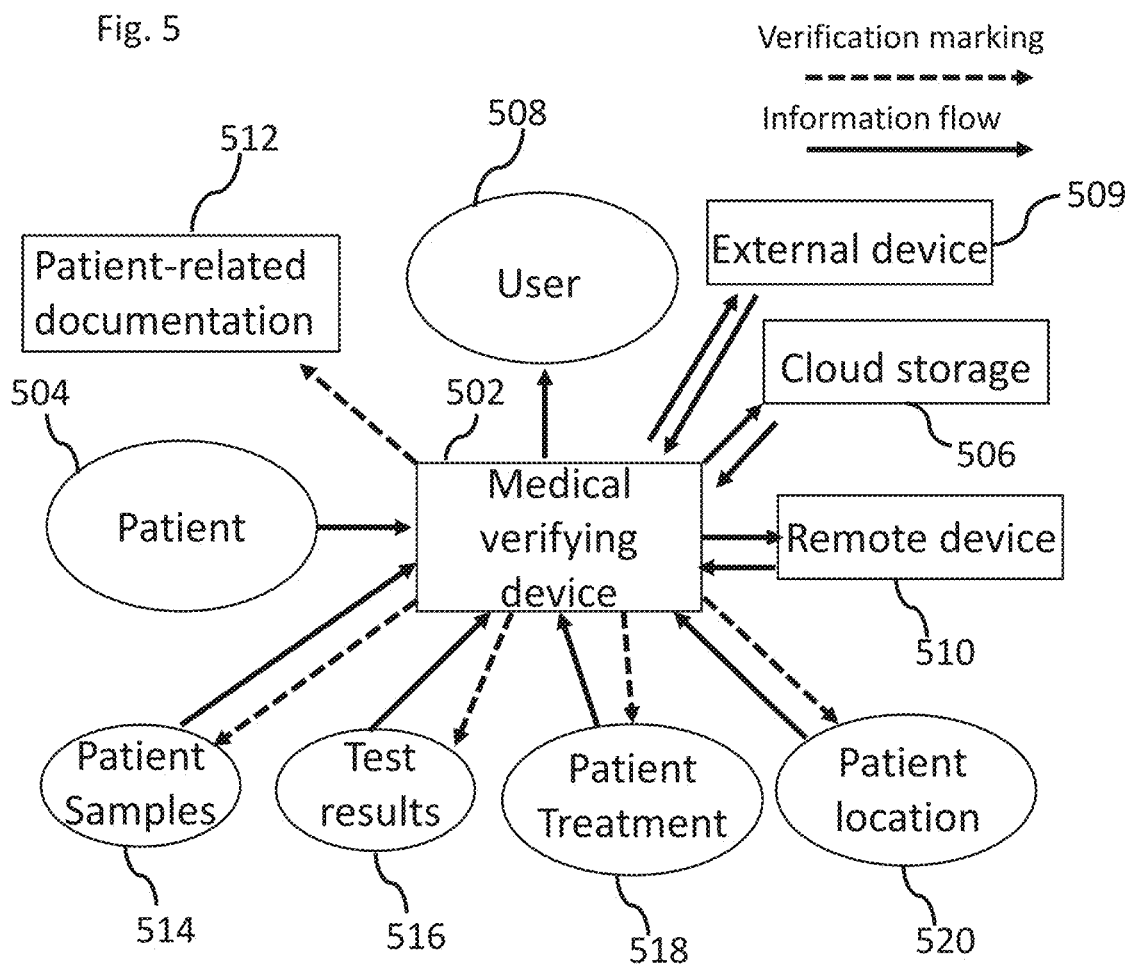
FIG. 5 is a schematic illustration showing interactions of a medical ID verifying device, according to some exemplary embodiments of the invention.

According to some exemplary embodiments, the verifying device, for example a medical verifying device, is used by one or more medical personnel, for example a nurse, a physician and/or a caregiver when interacting with a patient and/or medical items related to the patient. Reference is now made to FIG. 5 depicting interactions between a verifying device, for example a medical verifying device and items in a medical environment, according to some exemplary embodiments of the invention.

According to some exemplary embodiments, an ID verifying device, for example a medical verifying device 502 receives information, for example an ID indication from a patient 504. In some embodiments, the device 502 is configured to read information from a patient 504 by reading an ID tag attached to the patient and/or information stored in at least one memory circuitry associated with the patient, for example an RFID tag.

According to some exemplary embodiments, the device 502 reads information, for example at least one ID indication, related to one or more patient samples 514. In some embodiments, the patient samples comprise tissue samples and/or derivatives of tissue samples related to the patient 504. In some embodiments, the patient samples comprise, blood samples, urine samples, DNA samples, biopsy samples, stool samples or any other tissue samples and derivatives thereof related to the patient 504. In some embodiments, the patient samples information is read from a tag associated with a storing compartment of the samples, for example a tube, a cup, a vial, a bag, a box, a bottle or any other storage compartment of tissue samples.

According to some exemplary embodiments, the device 502 is configured to mark the tissue sample and/or the storage compartment of the tissue sample. In some embodiments, the device 502 marks the tissue sample and/or the storage compartment with one or more of an ink stamp, a sticker printed by the device 502 or with a printed marking, printed directly on the tissue sample or a surface associated with the storage compartment.

According to some exemplary embodiments, a user 508 of the device 502 reads an ID indication of the patient 504 and an ID indication of a tube containing a tissue sample. In some embodiments, the device 502 determines whether a relation between the two ID indications is a desired relation, for example if a determined relation between the two ID indications indicates that the tissue sample within the tube is derived from the patient. In some embodiments, if the relation is a desired relation then the tube is marked with a verification marking. In some embodiments, prior to testing the tissue sample in a remote testing facility, the verification marked is checked. In some embodiments, in case there is no verification marking on the tube, the tissue sample is not tested or discarded.

According to some exemplary embodiments, the device 502 reads information, for example at least one ID indication, related to one or more test results 516. In some embodiments, the test results 516 are related to the patient 504. In some embodiments, the test results comprise results of one or more of blood tests, urine tests, stool tests, imaging tests, for example X-RAY, MRI, CT imaging techniques results, DNA tests results, and/or biopsy tests results. In some embodiments, the device reads the information from a tag associated with the test results, for example with media storage of the test results. In some embodiments, the media storage comprises a disk on key, a memory circuitry, a CD or any other media storage device. Alternatively or additionally, the device 502 reads information stored with documentation associated with the test results.

According to some exemplary embodiments, the device 502 is configured to mark the test results 516 and/or the media storage or documentation of the test results 516. In some embodiments, the device 502 marks the test results 516 and/or the media storage or documentation of the test results 516 with one or more of an ink stamp, a sticker printed by the device 502, and/or with a printed marking, printed directly on the test results related documentation or on the media storage of the test results 516.

According to some exemplary embodiments, a user 508 of the device 502, for example a physician, receives a storage media, for example a USB disc-on-key or a CD-ROM with test results of a patient. In some embodiments, the user 508 reads an ID indication of the patient 504 and an ID indication of the storage media with the test results. In some embodiments, if the relation between the two ID indications is a desired relation, then the user 508 marks the storage media with a verification marking.

According to some exemplary embodiments, the device 502 reads information, for example at least one ID indication, related to a patient treatment 518. In some embodiments, the patient treatment is related to the patient 504. In some embodiments, the patient treatment 518 comprises bio active agents, for example one or more pharmaceutical drugs, or storage compartments of the bio active agents, for example bioactive agents which are part of a treatment protocol of patient 504. In some embodiments, the device 502 reads the information from a tag associated with a patient treatment 518 storage compartment or with documentation of the patient treatment. In some embodiments, the storage compartment of the patient treatment comprises a tube, a cup, a vial, a bag, a box, a bottle or any other storage compartment of bioactive agents. In some embodiments, the documentation of the patient treatment comprises invitations to perform a treatment, for example radiotherapy treatment, chemotherapy treatment, pharmaceutical treatment, a surgery, a transplantation surgery or any other treatment.

According to some exemplary embodiments, the device 502 is configured to mark documentation associated with the patient treatment 518 and/or a storage compartment of the patient treatment 518, for example storage compartment of bioactive agents. In some embodiments, the device 502 marks the patient treatment documentation and/or storage compartment with one or more of an ink stamp, a sticker printed by the device 502, and/or with a printed marking, printed directly on the patient treatment related documentation or on the storage compartment of the patient treatment 518.

According to some exemplary embodiments, a user 508 of the device 502, for example a nurse or any other caregiver reads an ID indication of the patient 504 and an ID indication on a storage compartment of a bioactive compound, for example a drug. In some embodiments, if a determined relation between the two ID indications is a desired relation, then the storage compartment is marked with a verification marking. In some embodiments, only when a verification marking is present on the storage compartment, the nurse is allowed to give the bioactive compound to the patient 504.

According to some exemplary embodiments, the device 502 reads information, for example at least one ID indication, related to a patient location 520. In some embodiments, the patient location 520 is a location to which the patient is transported, for example when a patient is transported to a selected ward, to a treatment location, to an analysis location or to any location related to the patient disease or treatment. In some embodiments, the device 502 reads an ID indication associated with the location, for example by reading a tag near or at the location. In some embodiments the device reads an ID indication of the patient 504 and determines whether a relation between the location ID indication and the patient ID indication is a desired relation. In some embodiments, if the relation is a desired relation, then the device 502 marks a patient ID tag, a patient-related documentation 512, a location tag and/or location documentation with a verifying marking.

According to some exemplary embodiments, the device 502 delivers one or more indications to the user 508 regarding a determined relation between the patient 504 and one or more of the patient samples 514, the test results 516, the patient treatment 518 and/or the patient location 520. Alternatively or additionally, the device 502 transmits one or more indications or signals to a remote device 510 and/or to a cloud storage 506, for example with regard to the determined relation between the two ID indications. Optionally, the device 502 uses one or more algorithms and/or look up tables stored in the remote device 510 and/or the cloud storage 506 during the verification process. In some embodiments, the cloud storage 506 and/or the remote device 510 store information, for example indication about one or more of ID indications, procedure protocol, procedure instructions. In some embodiments, the ID verifying device, for example the medical verifying device 502 determines a relation between an ID indication acquired by the device 502 and at least one indication, protocol or instructions stored in the cloud storage 506 and/or remote device 510. In some embodiments, the device 502 marks patient-related documentation with a verification marking if the determined relation is a desired relation between the two or more ID indications.

According to some exemplary embodiments, the device is in communication with an external device 509. In some embodiments, the external device comprises a machine used in a process that is verified by the medical verifying device 502. Alternatively or additionally, the external device comprises a device that is used in a medical, clinical and/or patient related procedure where the ID verifying device is used. In some embodiments, the medical verifying device 502 receives and/or transmits information and data to and from the external device. In some embodiments, operation of the medical verifying device, for example ID reading and/or marking is based on information received from the external device 509.

Exemplary markers of a verifying device According to some exemplary embodiments, the verifying module comprises a marker which is configured to generate a marking, for example a verification marking. Alternatively or additionally, the marker is configured to directly or indirectly mark an item. Reference is now made to FIGS. 6A-6D depicting verifying devices with different markers, according to some exemplary embodiments of the invention.

Figure 6A:
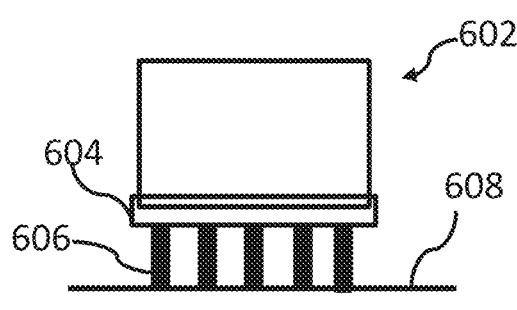
FIGS. 6A-6D are schematic illustrations of a verifying device with different optional markers, according to some exemplary embodiments of the invention.

According to some exemplary embodiments, for example as shown in FIG. 6A, a verifying device, for example verifying device 602 comprises a stamping marker, for example as in the JetStamp of REINER. In some embodiments, the stamping marker comprises a stamp 604, for example a self-inking stamp. In some embodiments, the stamp 604 comprises one or more marking heads, for example marking head 606, shaped and sized to stamp a portion of a surface 608. In some embodiments, the stamp 604 comprises an ink pad or an ink storage compartment. Optionally, the ink pad is placed in contact with one or more of the marking heads of the stamp, for example when the stamp is not in use. In some embodiments, the ink pad or ink chamber comprises ink that is visible to a naked eye of a human subject. Alternatively, ink pad or ink chamber comprises ink which is visible to a naked eye of a human subject if the ink is illuminated with light having selected one or more wave lengths.

According to some exemplary embodiments, the stamp, for example a rotating stamp comprises two or more interchangeable marking heads. In some embodiments, the stamp 604 is connected to a motor, for example an electric motor, configured to rotate the stamp. In some embodiments, rotation of the stamp places a different marking head in front of the surface 608.

Figure 6B:
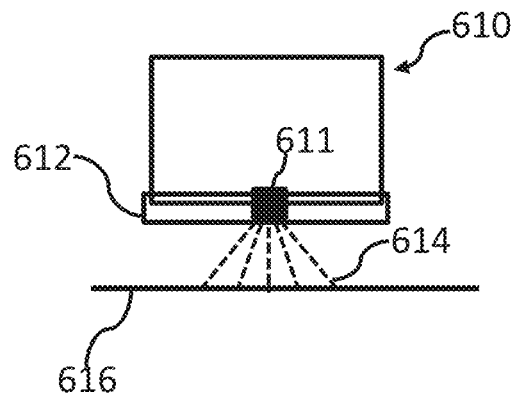

According to some exemplary embodiments, for example as shown in FIG. 6B, a verifying device, for example verifying device 610 comprises a light marker 612. In some embodiments, the light marker 612 comprises one or more light sources 611 which are configured to emit light beams 614 at a surface 616. In some embodiments, the one or more light sources 611 comprises a laser light source. In some embodiments, the laser light source is configured to mark an item by emitting laser beams at the surface 616 with sufficient energy to place a mark on the surface 616.

Figure 6C:
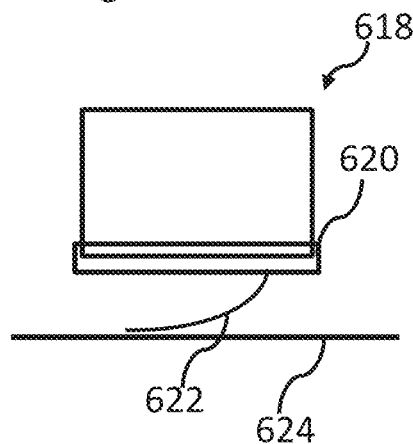

According to some exemplary embodiments, for example as shown in FIG. 6C, a verifying device, for example verifying device 618 comprises a printer 620, for example an inkjet printer or a sticker printer. In some embodiments, the printer 620 prints stickers, for example sticker 622 that can be directly attached to a surface 624 of an item. Alternatively, the ink jet printer comprises a pocket inkjet printer, for example the Speed-i-Jet 798 Portable pocket printer by REINER, configured to print directly on the surface 624.

Figure 6D:
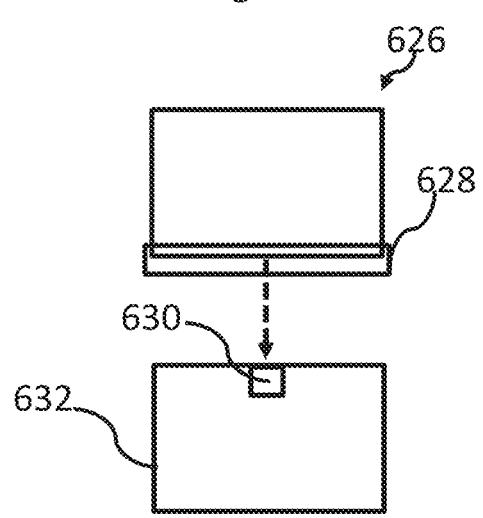

According to some exemplary embodiments, for example as shown in FIG. 6D, a verifying device, for example verifying device 626 comprises an electronic signaling marker, for example an RFID writer 628. In some embodiments, the RFID writer is a RFID reader. In some embodiments, the RFID writer is configured to electronically mark an item 632 by writing a verifying electronic indication into an RFID tag 630 of the item 632.

Exemplary Verifying Stamp

Figure 7A:
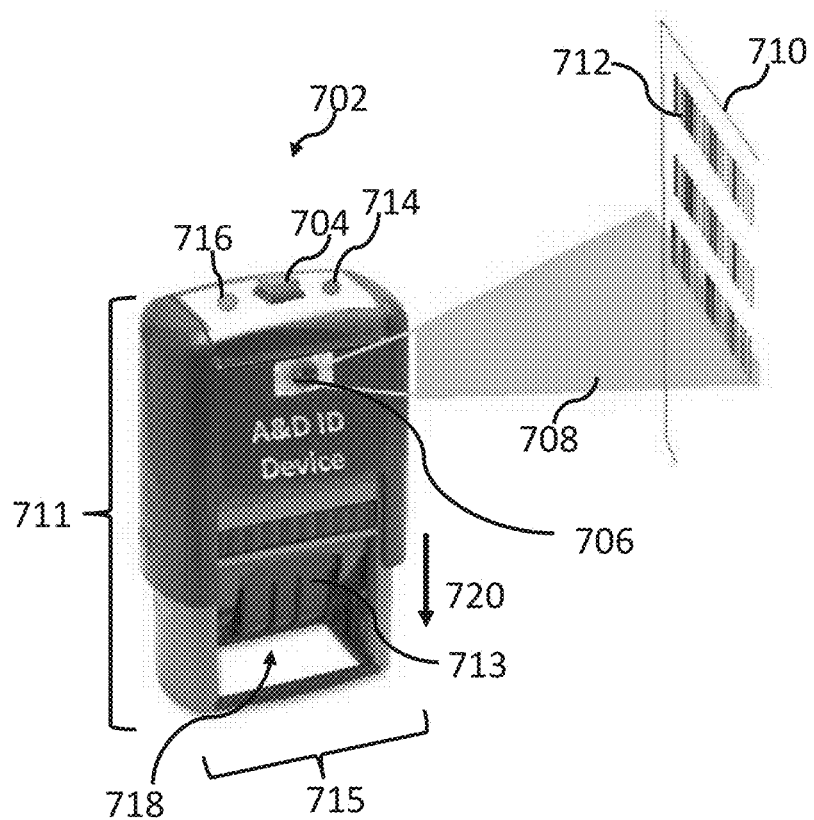
FIGS. 7A-7C are schematic illustrations of a verifying device comprising a stamp, according to some exemplary embodiments of the invention.

According to some exemplary embodiments, the verifying device comprises a stamp, for example a self-inking stamp, and an ID reader. In some embodiments, a user, for example a medical personnel user, uses the self-inking stamp without verifying an ID indication. In some embodiments, the user uses the self-inking stamp to mark an item with a marking which includes an ID indication of the user, for example with a marking which includes ID details of the user. In some embodiments, when the verifying device is used to verify a desired relation between two or more ID indications, the stamped marking is modified to include a verification marking in addition to the ID indication of the user. Alternatively, the stamped marking is modified to include a verification marking instead of the ID indication of the user. Reference is now made to FIG. 7A depicting a verifying device comprising a stamp, according to some exemplary embodiments of the invention.

According to some exemplary embodiments, a verifying device, for example verifying device 702 comprises a stamp 718, for example a self-inking stamp. In some embodiments, the stamp 718 is configured to mark a surface by pressing a marking head 713 of the device 702 in direction 720 towards the surface. In some embodiments, the device comprises a lock configured to prevent the pressing of the marking head 713 against the surface.

According to some exemplary embodiments, the verifying device comprises an ID reader 706. In some embodiments, the ID reader is configured to read a code, for example a code 712 located on a surface 710, and positioned within a field of view 708 of the ID reader 706. In some embodiments, the ID reader comprises an optic sensor, for example a camera, which is configured to capture an image and/or information presented as a 2D code or a 3D code, positioned within a field of view of the camera.

According to some exemplary embodiments, the verifying device 702 comprises a user interface for receiving input from a user of the device and/or for delivering of one or more human detectable indications to a user of the device. In some embodiments, the user interface comprises at least one button 704. In some embodiments, the button 704 is used for activation of one or more of the functions of the device 702, for example activation of the ID reader 706. Alternatively or additionally, the at least one button 704 is used for selecting one or more activation options of the device 702.

According to some exemplary embodiments, the user interface comprises one or more indicators, for example audio and/or visual indicators, configured to generate a human detectable indication to a user of the verifying device 702. In some embodiments, the one or more indicators comprise at least one light source configured to deliver a visual indication, for example light indicators 714 and 716 of the device 702. In some embodiments, at least one light indicator is a positive light indicator configured to deliver a positive indication, for example by emitting green light. In some embodiments, at least one light indicator is a negative light indicator, configured to deliver a negative indication, for example by emitting red light.

According to some exemplary embodiments, the one or more indicators deliver a positive indication, for example when an ID indication is read, when a relation between two or more ID indications is a desired indication, and/or when a marking of an item is performed, for example by the stamp 718. Alternatively or additionally, the one or more indicators deliver an alert signal, for example when a determined relation between two or more ID indications is not a desired indication, and/or when an item is not marked within a predetermined time period. Alternatively or additionally, the one or more indicators deliver an alert signal to a user of the device, for example when an ID indication is not read within a predetermined time duration. In some embodiments, the one or more indicators deliver an indication to a user of the device with regard to a locking state of the lock, for example when the lock is active and/or when the lock is inactive.

According to some exemplary embodiments, the device, for example device 702 is shaped and sized to be held by a single hand of an adult subject. In some embodiments, a maximal length of the device, for example length 711 is in a range of 5-17 cm, for example 5-10 cm, 8-12 cm, 11-17 cm or any intermediate, smaller or larger range of values. In some embodiments, a maximal width of the device 702, for example width 715, is in a range of 3-10 cm, for example 3-8 cm, 5-9 cm, 6-10 cm or any intermediate, smaller or larger range of values. In some embodiments, a maximal weight of the device 702 is in a range of 30-300 gr, for example 30-150 gr, 100-200 gr, 180-300 gr or any intermediate, smaller or larger range of values.

Figure 7B:
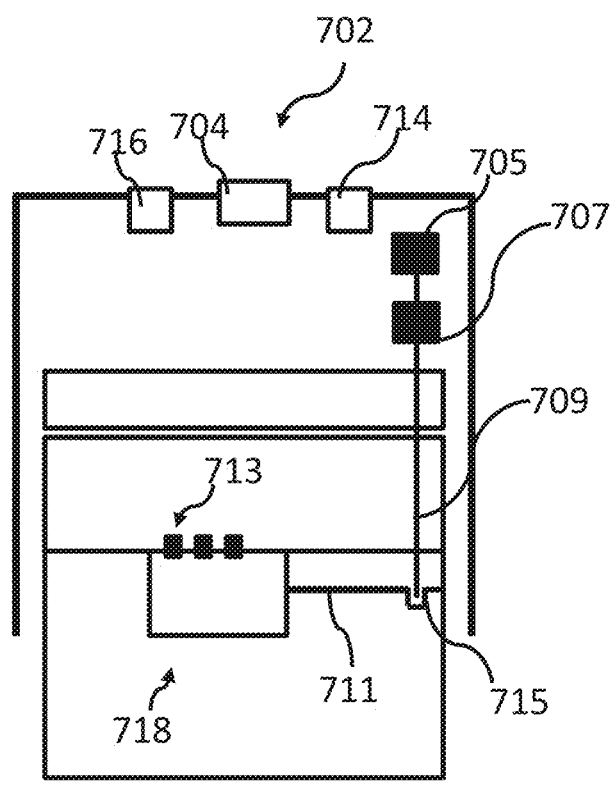

Reference is now made to FIG. 7B depicting a stamp lock, according to some exemplary embodiments of the invention.

According to some exemplary embodiments, the device 702 comprises a stamp lock comprising at least one actuator 707 for example an electrical actuator electrically connected to a power source 705. In some embodiments, the stamp lock interferes, for example mechanically interferes with a rotation of the stamp 718. In some embodiments, the stamp lock prevents the rotation of the marking head 713, and therefore, optionally, prevents the interaction between the marking head and a surface. In some embodiments, the actuator 707 control the movement of a locking bar 709, which is shaped and sized to lock and unlock the movement of the stamp, for example the rotation of the stamp 718. In some embodiments, at least a portion of the locking bar 709 is shaped and sized to fit into a recess within a rotation mechanism of the stamp, for example into recess 715 of a rotating bar 711 connected to the stamp 718.

According to some exemplary embodiments, rotation of the rotating bar rotates the stamp 718 and the marking head 718. In some embodiments, insertion of at least a portion of the locking bar into the recess 715 prevents the rotation of the stamp 718, for example by mechanically interfering with the rotation of the rotating bar. In some embodiments, when a signal is received from a control unit of the device 702, the actuator 707 retracts the locking bar 709 from the recess 715. In some embodiments, retraction of the locking bar 709 allows the rotation of the stamp 718.

Figure 7C:
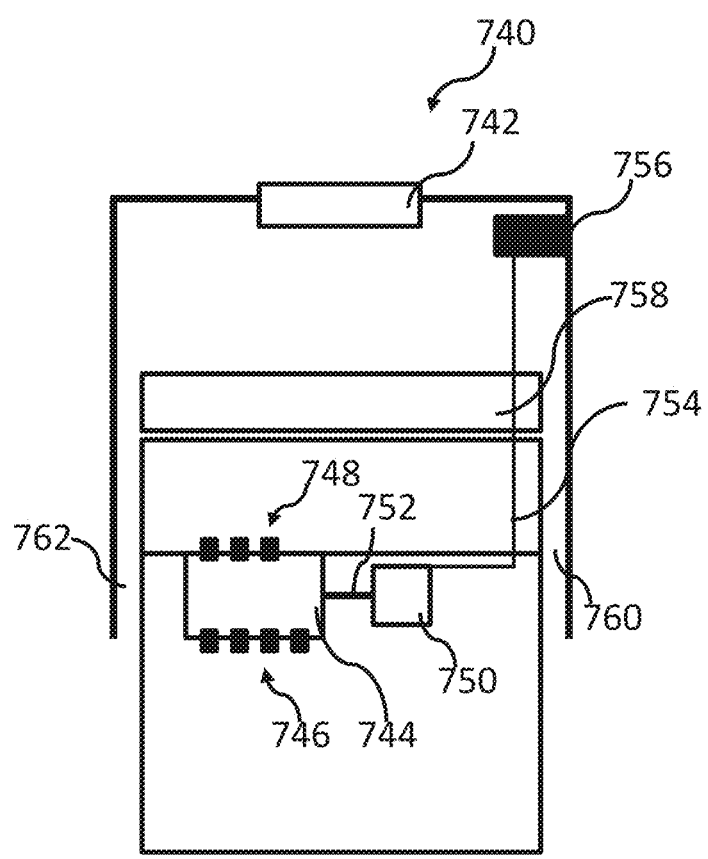

Reference is now made to FIG. 7C depicting a verifying device with a stamp having two or more marking heads, according to some exemplary embodiments of the invention.

According to some exemplary embodiments, a verifying device, for example device 740 comprises a stamp 744, for example a rotating stamp. In some embodiments, the stamp 744 comprises two or more marking heads for example marking heads 746 and 748. In some embodiments, the stamp 744 is a self-inking stamp. In some embodiments, the device 740 comprises an ink storage compartment, for example an ink pad 758 which is configured to be in contact with at least one of the marking heads.

According to some exemplary embodiments, the device 740 comprises an actuator 750, for example an electrical actuator, functionally connected to the stamp 744 via bar 752. In some embodiments, actuator 750 is electrically connected to a power source 756 via electrical wiring 754. Additionally, the device 740 comprises at least one ID reader, for example ID reader 742 configured to read one or more ID indications. In some embodiments, the ID reader is similar to ID reader 206 shown in FIG. 2A.

According to some exemplary embodiments, the device 70 is a multi-action device, configured to mark an item with a first marking head, and following verification to mark the same item or a different item with a different marking head. In some embodiments, when the ID reader 742 is not operated, the verification function of the device 740 is inactive. In some embodiments, when the verification function is inactive, the device 740 marks an item with a first marking head, for example marking head 748. In some embodiments, when the ID reader 742 is activated, but a desired relation is not verified, the device 740 marks an item with the first marking head, for example marking head 748. Alternatively, when the ID reader 742 is activated and a desired relation between two ID indications is verified, the actuator 750 is activated and rotates the stamp 744, for example to allow marking of an item with a different marking head, for example marking head 746. In some embodiments, the different marking head contains an additional mark compared to the first marking head, for example the verification mark.

Reference is now made to FIGS. 7D-7G, depicting an ID verifying device which comprises a stamp, according to some exemplary embodiments of the invention.

According to some exemplary embodiments, an ID verifying device, for example device 770 comprises a marking module, for example a stamp 772. Alternatively or additionally, the marking module comprises an engraver, or a printer, for example a laser or an ink printer. In some embodiments, the marking module is configured to mark a surface with a reversible or a removable marking. Alternatively, the marking module is configured to mark a surface with a permanent marking, for example a marking that includes information that is visible or readable for at least 2 months, for example at least 6 months, at least 12 months, at least 2 years or any intermediate, shorter or longer time periods, without applying external force on the marking.

According to some exemplary embodiments, the marking module is configured to move between an active state, in which marking of a surface is possible, and an inactive state, in which marking of the surface is not possible. In some embodiments, the ID verifying device comprises a marking module controller, configured to control an activation state of the marking module. In some embodiments, the marking module controller comprises a locker, for example locker 774. Optionally, locker 774 is an electrical locker. In some embodiments, the locker is configured to lock the marking module in a specific position and/or orientation that prevents contact and/or alignment with a surface. Alternatively, the marking module controller comprises a cover configured to cover or block the marking module in a way that prevents interaction between the marking module, for example the stamp 772 and a surface.

According to some exemplary embodiments, the ID verifying device, for example device 770 comprises an ID reader, which is configured to read identity related information. In some embodiments, the ID reader comprises image acquisition module 776. In some embodiments, the image acquisition module comprises an optic sensor, configured to obtain an image which includes ID-related information. In some embodiments, the image acquisition module 776 comprises a code reader, for example a barcode reader, a two-dimensional code reader, and/or a three-dimensional code reader. Optionally, the optic sensor is part of the code reader. In some embodiments, a housing 778 of the device 770 comprises an opening 780, which is optionally aligned with an optic sensor of the image acquisition module 776, for example to allow image acquisition through the casing 778. In some embodiments, the opening 780 comprises a transparent cover, which is optionally a lens.

According to some exemplary embodiments, the ID verifying device, for example device 770 comprises a communication port 781, for example a universal serial bus (USB) port, which is configured to allow connection of the ID verifying device to a different device, to a data storage component, and/or to an electric charger.

According to some exemplary embodiments, the ID verifying device, for example device 770 comprises an activation switch 783, configured to activate the device 770, for example without initiating a verification process.

According to some exemplary embodiments, the ID reader comprises a radiofrequency (RF) reader, for example a RFID tag reader, configured to receive an identity indicative radio signal.

According to some exemplary embodiments, the ID verifying device, for example device 770 comprises a control circuitry, for example control circuitry 782. In some embodiments, the control circuitry is electrically connected to a memory of the device 770. In some embodiments, the control circuitry is electrically connected to the ID reader, which comprises the image acquisition module 776. In some embodiments, the control circuitry 782 is electrically connected to the marking module of the device 770 and/or to the locker, for example locker 774.

According to some exemplary embodiments, the device 770 comprises a user interface, configured to receive input from a user of the device 770, for example from a physician, a nurse, a clinician, a pharmacist, a laboratory worker or any other person working in a hospital or a clinic, or any other person working with patients. In some embodiments, the user interface is electrically connected to the control circuitry 782. In some embodiments, the user interface comprises at least one button, for example an activation button 784, or a touch sensor, configured to receive a signal from the user based on a force applied by the user on the sensor. Optionally, the user interface comprises a microphone, which is configured to record audio signals from the vicinity of the device 770 and/or from a user of the device.

According to some exemplary embodiments, the user interface comprises one or more signal generators, for example light signal and/or audio signal generators. In some embodiments, the one or more signal generators are configured to deliver an indication, for example a human detectable indication to a user of the device. Optionally, the indication comprises an alert signal. In some embodiments, the one or more signal generators comprise a speaker configured to generate audio signals. Alternatively or additionally, the one or more signal generators comprise at least one light emitter, for example light emitting diode (LED) 786.

According to some exemplary embodiments, the device 770 comprises a communication circuitry, configured to transmit and/or receive signals from at least one other device, for example an ID verification device, a remote computer, a cellular device, a cloud storage, and/or a remote server. In some embodiments, the communication circuitry is electrically connected to the control circuitry 782. In some embodiments, the signals comprise wireless signals, for example radio signals, Bluetooth signals, Wi-Fi signals, infrared signals or any other non-wired signal.

According to some exemplary embodiments, the device 770 comprises at least one position and/or orientation senor, electrically connected to the control circuitry 782. In some embodiments, the position sensor comprises a global positioning system module configured to receive and/or transmit information related to the position of the device 770 in a room, in a clinic, in a hospital or in any other defined 3D environment. In some embodiments, the orientation sensor comprises an accelerometer and/or a gyroscope, configured to sense an orientation of a sensor relative to an external x-y-z coordinate system, for example a fixed coordinate system. In some embodiments, the orientation sensor is configured to sense yaw, tilt and/or roll of the device 770, for example around at least one axis of the device. In some embodiments, the device 770 comprises a proximity sensor, configured to sense a proximity of the device 770 to a patient and/or to an ID tag or marking.

According to some exemplary embodiments, the control circuitry 782 is configured to activate the ID reader, for example to activate the image acquisition module 776 and/or to activate the RF reader, when receiving a signal from the user of the device, for example via the user interface circuitry. Alternatively or additionally, the control circuitry 782 is configured to activate the ID reader, optionally automatically, based on a position and/or orientation of the device 770. Alternatively or additionally, the control circuitry 782 is configured to activate the ID reader based on a proximity to an ID tag.

According to some exemplary embodiments, the device 770 is configured to acquire ID information, for example from an ID tag, optionally using the ID reader. In some embodiments, the control circuitry 782 determines a relation between the acquired ID information and at least one indication stored in a memory of the device 770. In some embodiments, the stored indication is an indication of an ID information. Alternatively, the control circuitry 782 transmits the acquired ID information to a remote device using the communication circuitry of the device 770. In some embodiments, the remote device determines a relation between the acquired ID information and at least one indication stored in the remote device. In some embodiments, the remote device transmits the results of the relation determining process to the control circuitry 782 of the device 770, for example using the communication circuitry. Alternatively or additionally, the control circuitry 782 determines a relation between the acquired ID information and at least one indication stored in the remote device.

According to some exemplary embodiments, if the determined relation is a desired determined relation, then the control circuitry 782 allows marking, for example marking of a surface, using the marking module, for example using the stamp 772. In some embodiments, if the determined relation is a desired relation, then the control circuitry 782 activates the marking module. Alternatively or additionally, if the determined relation is a desired relation then the control circuitry 782 unlocks the locker 774, for example to allow activation of the marking module. In some embodiments, unlocking the locker 774 allows, for example, interaction and/or alignment between the marking module, which optionally comprises a stamp 772, and a surface. Alternatively or additionally, if the determined relation is a desired relation then the control circuitry 782 removes a cover which prevents interaction between the marking module and a surface.

According to some exemplary embodiments, for example as shown in FIG. 7G, the device, for example device 770 comprises a movable portion 788 including the stamp 772, which is configured to move with respect to a stationary portion 790, during marking. In some embodiments, locker 774 is configured to lock the movable portion 788 in a stationary position relative to the stationary portion 790, for example to prevent marking. In some embodiments, the control circuitry 782 is configured to unlock locker 774 to allow marking, for example by allowing movement of the movable portion 788 relative to the stationary portion 790. In some embodiments, movement of the movable portion 788 allows marking, for example by allowing contact between the stamp 772 and a surface.

According to some exemplary embodiments, the device, for example device 770 is configured to authenticate an identity of a user. In some embodiments, the device 770 comprises a fingerprint reader configured to read a fingerprint of a user, for example prior to activation of the device 770 or prior to marking. Alternatively or additionally, the device 770 is configured to use the ID reader to authenticate the user identity. In some embodiments, the device, for example device 770, is configured to authenticate the user identity based on a relation between the user acquired fingerprint, acquired user biometrics or any other acquired information related to the user identity, and at least one indication stored in a memory of the device 770. Alternatively or additionally, the device is configured to authenticate the user identity based on a relation between the user acquired fingerprint, acquired user biometrics or any other acquired information related to the user identity, and at least one indication stored in a remote device, for example a server, a cloud storage or a network. In some embodiments, the device 770 connect an application on a remote device, a cloud storage and/or a network using the communication circuitry to authenticate the user ID, for example to verify that the user of the device, for example a caregiver, caregiver is allowed to perform a treatment, prescribe medication by optionally linking between a preset array of permissions of the user and the intended treatment.

According to some exemplary embodiments, if the user identity authentication fails, the device, for example device 770 prevents the use of the marking module. Optionally, an alert signal is transmitted to a remote device. In some embodiments, the device, for example device 770, prevents prescription of contraindicative medications or treatment if the user authentication fails.

According to some exemplary embodiments, marking requires receiving an approval signal from two or more sources, one from the device, for example device 770, and an additional approval signal from an additional source, for example from a remote device, for example a different ID verifying device or from a different user.

According to some exemplary embodiments, the memory of the device, is configured to store log files, and/or ID indications. In some embodiments, access to the memory of the device is allowed when receiving a specific permission to access the content of the memory, and/or when the device is in a specific activation state.

Alternatively, the log files are stored in a memory of a remote device, for example in an application of a cellular device, in a remote computer, and/or in a remote server or cloud storage. In some embodiments, the remote server or a cloud storage comprise a remote server or a cloud storage of a medical facility, for example a hospital or a clinic.

According to some exemplary embodiments, the ID verifying device, for example device 770 comprises an electric power source, for example at least one battery 775. In some embodiments, the battery 775 is a rechargeable battery. Optionally, the battery 775 is a removable battery. In some embodiments, the ID verifying device comprises a charging connector, for example a charging socket, configured to allow connection of an external electric charger to the ID verifying device.

Exemplary Marking Process

Figure 8A:
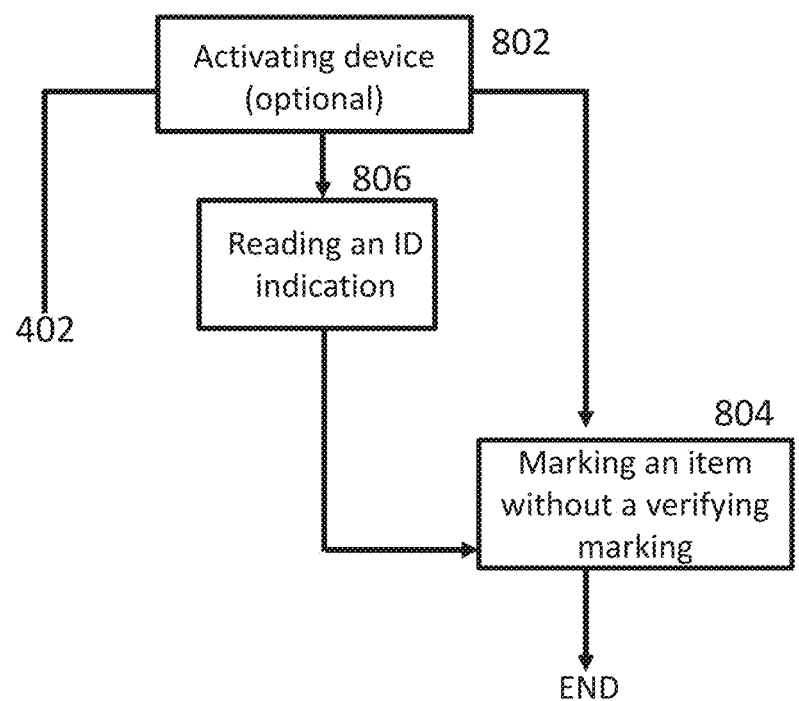
FIG. 8A is a flow chart of a process for activating a multifunction verifying device by a user, according to some exemplary embodiments of the invention.

According to some exemplary embodiments, a verifying device comprising a marker, for example a stamp, marks an item without verifying a relation between two ID indications. Reference is now made to FIG. 8A depicting a process of using a multifunction verifying device, according to some exemplary embodiments of the invention.

According to some exemplary embodiments, a user activates the verifying device at block 802. In some embodiments, the user activated the verifying device by interacting with a user interface of the verifying device. Alternatively, the verifying device is automatically activated when a user moves the device, for example changes a location of the device and/or lifts the device from a surface.

According to some exemplary embodiments, a user marks an item without a verifying marking using the verifying device at block 804. In some embodiments, the user marks the item with an ID marking, for example an ID marking with identification details of the user, for example identification details of a physician or any other medical personnel.

According to some exemplary embodiments, a user reads an ID indication at block 806. In some embodiments, the user reads an ID indication after activating an ID reader of the device. Alternatively or additionally, the user reads an ID indication after selecting an option for ID reading using a user interface of the device. Alternatively, the user reads an ID indication by pointing an ID reader of the device towards an ID indication mark, for example a barcode or a QR code.

According to some exemplary embodiments, after reading an ID indication, the user marks an item without a verifying marking at block 804, as described above.

According to some exemplary embodiments, a user reads two ID indications, for example a first ID indication and a second ID indication, for example as describes in block 402 and 404 shown in FIG. 4.

Figure 8B:
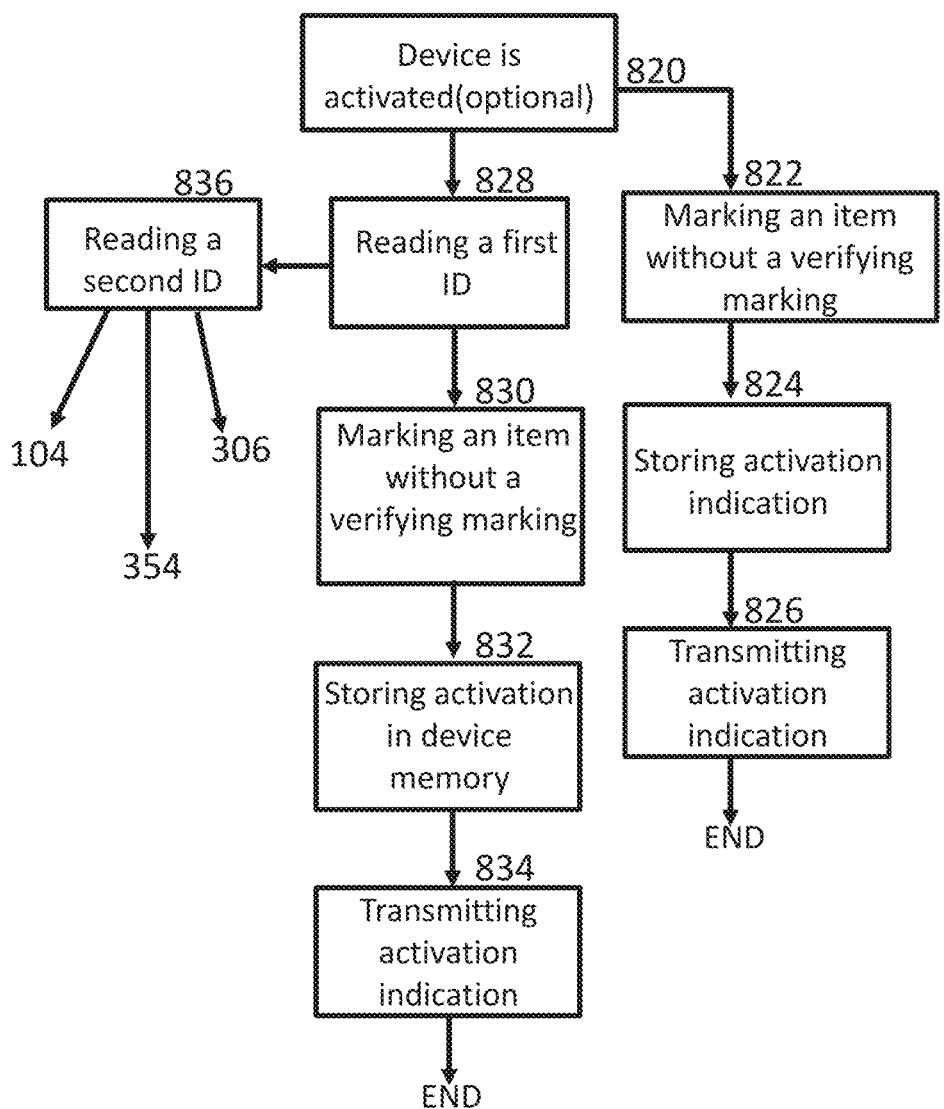
FIG. 8B is a flow chart of an activation process of a multifunction verifying device, according to some exemplary embodiments of the invention.

Reference is now made to FIG. 8B depicting an activation process of a verifying device which operates with or without verification of a relation between two ID indications, according to some exemplary embodiments of the invention.

According to some exemplary embodiments, a verifying device is activated at block 820, for example the device shift from a stand-by mode to an active mode. In some embodiments, the device is activated when a user interacts with a user interface of the device, for example user interface 210 shown in FIG. 2A and/or push button 238 shown in FIG. 2B. Alternatively, the device automatically shifts to an active mode when an orientation of the device changes based on one or more signals received from orientation sensors, for example orientation sensor 224 shown in FIG. 2A.

According to some exemplary embodiments, the device marks an item without a verifying marking at block 822. In some embodiments, a marker of the verifying device, for example marker 214 or an external marker 218 is activated to mark the item at block 822. In some embodiments, the marker marks the item with a marking comprising one or more indications, for example ID indications, date and/or time indications, location indications or any other type of indication that does not relate to a verification indication. Optionally, the marking comprises one or more ID indications of a user of the device, for example name and/or an ID number of the user.

According to some exemplary embodiments, the device stores one or more activation indications at block 824. In some embodiments, the device stores an indication related to the marking performed at block 822. In some embodiments, the device stores the activation indication in a memory of the device, for example memory 208 shown in FIG. 2A or the memory 242 shown in FIG. 2B. In some embodiments, the one or more activation indications comprise one or more of information regarding the user identity performing the marking at 824, date, time, and/or location of the marking.

According to some exemplary embodiments, the device transmits one or more activation indication to a remote device at block 826. In some embodiments, the device transmits an indication related to the marking performed at block 822. In some embodiments, the device transmits the activation indication using a communication circuitry of the device, for example communication circuitry 212 shown in FIG. 2A. In some embodiments, the one or more transmitted activation indications comprise one or more of information regarding the user identity performing the marking at 824, date, time, and/or location of the marking. Optionally the transmitted indication comprises the activation indication stored at block 824. In some embodiments, the device transmits the one or more activation indications to a remote device comprising, a mobile device, a remote computer, a remote server and/or a cloud storage.

According to some exemplary embodiments, the device reads a first ID indication at block 828. Optionally, the device reads the first ID indication following activation of the device at block 820. In some embodiments, the device reads the first ID indication using the ID reader 206 shown in FIG. 2A or the code reader 240 shown in FIG. 2B.

According to some exemplary embodiments, the device marks an item at block 830. In some embodiments, the device marks the item with a marking that does not include a verifying marking, for example as described at block 822. Optionally, the marking comprises information regarding the user of the device and/or information regarding the reading of the first ID indication at block 828.

According to some exemplary embodiments, the device stores at least one indication, for example an activation indication at block 832. In some embodiments, the at least one stored indication comprises information regarding the reading of the first ID indications and/or the marking performed at block 830. In some embodiments, the device stores the at least one indication in a memory of the device, for example memory 208 shown in FIG. 2A or the memory 242 shown in FIG. 2B. In some embodiments, the device stores the at least one indication as described previously at block 824.

According to some exemplary embodiments, the device transmits at least one indication, for example an activation indication at block 834. In some embodiments, the device transmits the at least one indication as described previously at block 826. In some embodiments, the transmitted indication comprises information regarding the reading of the first ID indications and/or the marking performed at block 830.

According to some exemplary embodiments, following the reading of the first ID indication at block 828, the device reads a second ID indication at block 836. In some embodiments, following the reading of the second ID indication at block 836, the device automatically verifies a relation between the two read ID indications, for example as described at block 104 shown in FIG. 1.

According to some exemplary embodiments, following the reading of the second ID indication at block 836, the device determines if a relation between the two read ID indications is a desired relation, for example as described at block 306 shown in FIG. 3A.

According to some exemplary embodiments, at least one ID indication of the first and second ID indications is stored as a Master ID indication in the memory of the device, and the second ID indication is stored as a Test ID indication. In some embodiments, the device determines a relation between the stored Master ID indication and the Test ID indication, for example as described at block 354 shown in FIG. 3B.

Exemplary Process Verification

Figure 9A:
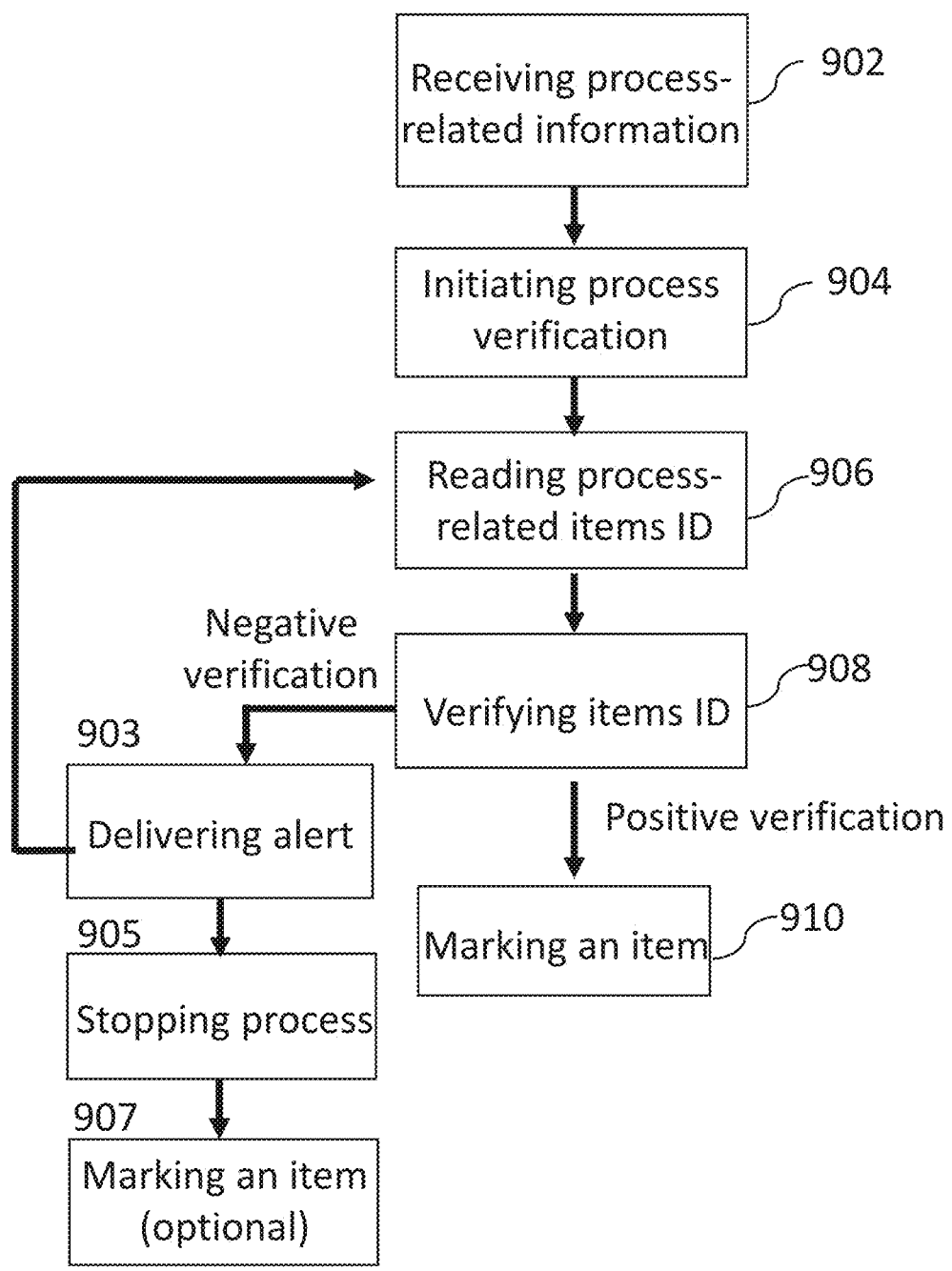
FIG. 9A is a flow chart of a process for verification of a procedure, according to some exemplary embodiments of the invention.

According to some exemplary embodiments, the ID verifying device is configured to monitor and verify a selected procedure, for example by verifying that a procedure protocol is followed. In some embodiments, a marker, for example a stamp, is activated or is allowed to be activated based on the results of the process verification procedure. Reference is now made to FIG. 9A, depicting a general scheme of a process verification procedure, according to some exemplary embodiments of the invention.

According to some exemplary embodiments, information related to a process is received at block 902. In some embodiments, the information is received by an ID verifying device, for example one of the devices 202, 502, 702, 740 or 770. In some embodiments, the process-related information is received by reading at least one ID tag, for example using an ID reader of the device. Alternatively or additionally, the process-related information is received via wireless signals transmission, for example Wi-Fi signals, Bluetooth signals, light signals, and/or radio frequency (RF) signals. In some embodiments, the received information is stored in the memory of the device.

According to some exemplary embodiments, the process-related information comprises a process ID or an ID of a product created using the process. Alternatively or additionally, the process-related information comprises a protocol of the process and/or parameters thereof, and/or values of protocol parameters.

According to some exemplary embodiments, a verification of the process is initiated at block 904. In some embodiments, the process verification is initiated once a protocol of the process is found in the memory of the device. In some embodiments, if the protocol is not found, then a protocol is downloaded, for example from a remote device, for example from remote computer, a remote server and/or a remote cloud storage. Alternatively, the process protocol is stored in a memory of the remote device.

According to some exemplary embodiments, ID of items related to the verified process are read, at block 906. In some embodiments, the process-related items comprise, for example, components or ingredients for the production of an object or a bioactive compound, for example a drug. Alternatively or additionally, the process-related items are items the need to be used during the process, for example according to the process protocol. In some embodiments, the ID of these items is read using the ID reader, and/or via wireless communication between the ID verifying device and the items.

According to some exemplary embodiments, an ID read by the device is verified at block 908. In some embodiments, during ID verification, a relation between the read ID and a stored protocol of the process or parameters and/or parameters values thereof, is determined. In some embodiments, if two or more IDs are read, then an order and/or a timing of the readings and/or each ID is verified, for example using the stored information.

According to some exemplary embodiments, if the verification is a positive verification, then an item associated with the process is marked at block 910. In some embodiments, the item is marked with a verification marking. Optionally, the verification marking is a quality assuring marking. In some embodiments, a quality assuring marking is a marking indicating that the process was performed according to a desired protocol and/or according to desired standards. In some embodiments, the item is a product formed by the verified process. Alternatively or additionally, the item comprises documentation associated with the process, for example a certificate.

According to some exemplary embodiments, if the verification is a negative verification, for example if the relation between the read ID and the stored protocol of the process or parameters and/or parameters values thereof is not a desired relation, then an alert signal is delivered at block 903. In some embodiments, the alert signal comprises a human detectable alert signal, configure to be detected by a human, for example a user of the ID verifying device. In some embodiments, the alert signal is a visual alert signal, for example activation of a light source indicating an alert signal, for example a LED.

According to some exemplary embodiments, if the verification is a negative verification, an additional attempt to read a process-related item ID is performed at block 906. In some embodiments, the additional attempt to read the process-related item ID is performed, for example when a wrong ID was read, and/or that a timing of the reading is not within a desired time window. Optionally, a user interface of the ID verifying device, for example a display, delivers information to the user of the ID verifying device regarding the negative verification.

According to some exemplary embodiments, if the verification is a negative verification, then the process is stopped at block 905. In some embodiments, the process is stopped, for example when the process cannot be continued, and needs to be restarted.

Optionally, an item associated with a stopped process is marked at block 907. In some embodiments, the item associated with the stopped process is marked with a marking indicating negative verification and/or an incomplete process. Alternatively or additionally, the marking indicates a product that does not meet a desired protocol and/or desired standards.

Exemplary Verification of a Drug Production Process

Figure 9B:
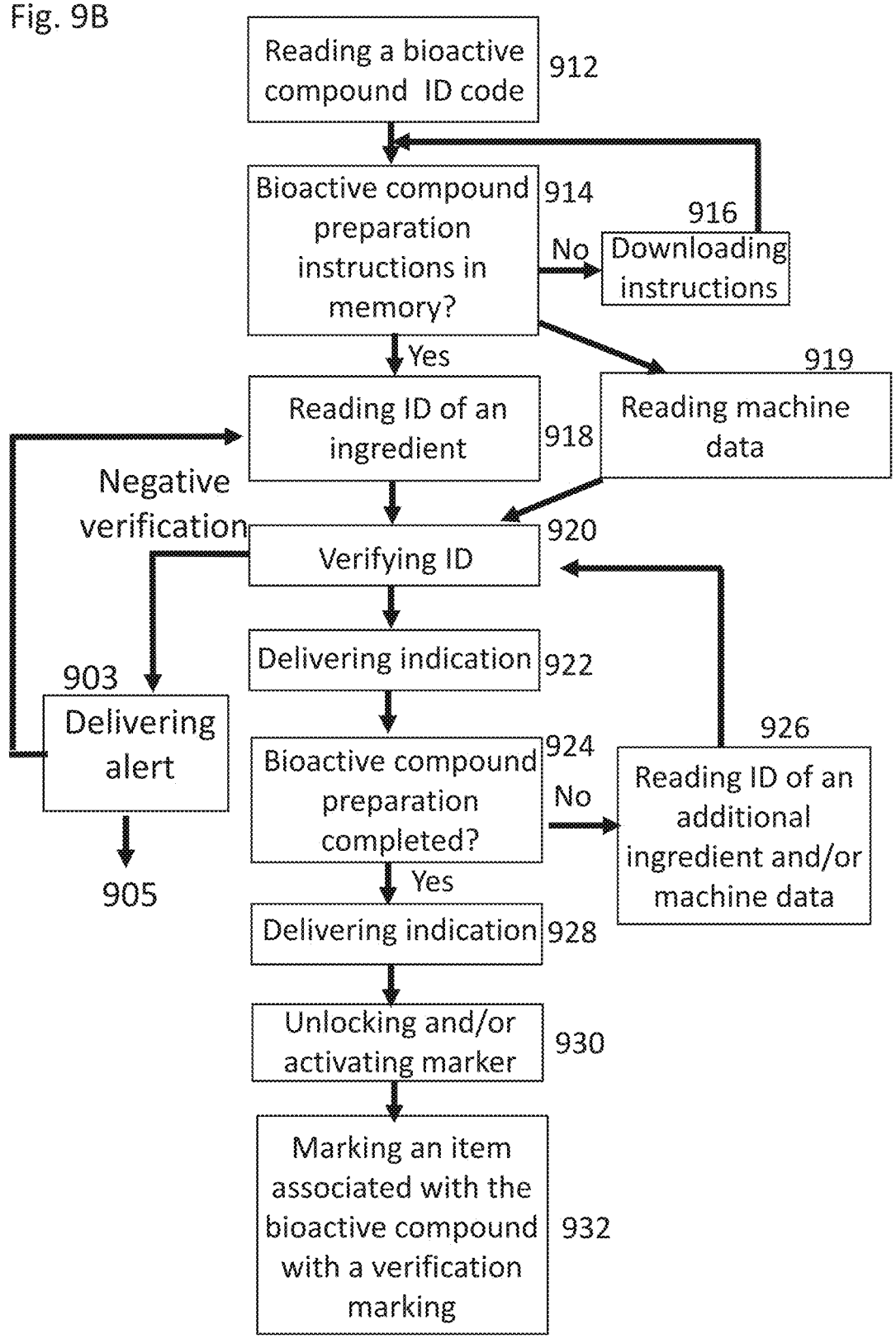
FIG. 9B is a flow chart of a process for verification of a procedure for the manufacturing of a bioactive compound, for example a drug, according to some exemplary embodiments of the invention.

According to some exemplary embodiments, the ID verifying device is used to verify that a bioactive compound, for example a drug, is prepared according to a desired protocol and/or according to desired standards, for example good manufacturing practice (GMP) standard, International Organization for Standardization (ISO) standard, or any other standard generated by a regulatory authority. In some embodiments, the ID verifying device is used to mark a product, for example the bioactive compound with a marking indicating that the product was manufactured according to an approved protocol and/or under approved conditions. Reference is now made to FIG. 9B, depicting a process for verification of a bioactive compound production procedure, according to some exemplary embodiments of the invention.

According to some exemplary embodiments, a bioactive compound ID code is read at block 912. In some embodiments, the ID code is read prior to initiation of a bioactive compound preparation procedure. In some embodiments, the ID code is read by an ID reader of the ID verifying device.

According to some exemplary embodiments, the ID verifying device determines a relation between the acquired ID code and information, for example instructions or a protocol of a procedure for preparation of the bioactive compound, that are stored in the memory of the ID verifying device, at block 914. In some embodiments, if a protocol does not exist in the memory of the ID verifying device an indication is delivered to a user of the ID verifying device, for example using the user interface of the device. Additionally, if the protocol does not exist in the memory of the ID verifying device, at least some of the instructions are downloaded from a remote device, for example a remote computer, a remote server, a remote cloud storage, at block 916.

According to some exemplary embodiments, if instructions, for example a protocol for preparation of the bioactive compound exist in the memory of the ID verifying device, an indication is delivered to a user of the ID verifying device. Additionally or alternatively, a verifying process is initiated, for example by reading an ID of a component in the manufacturing process, for example an ID of an ingredient, at block 918.

According to some exemplary embodiments, machine data is acquired at 919. In some embodiments, data from a machine, for example an external device that is used during the bioactive compound preparation, is acquired at block 919. In some embodiments, the machine comprises a mixer, an oven or any other device used in the manufacturing of the bioactive compound.

According to some exemplary embodiments, a relation between the acquired ingredient ID and the stored instructions is determined at block 920, for example as part of a verification process to make sure that the ingredient associated with the ingredient ID is part of the protocol for preparation of the bioactive compound. In some embodiments, if the relation between the acquired ingredient ID and the stored protocol is not a desired relation, the verification is a negative verification, and an alert signal is delivered at block 903, for example as described in FIG. 9A. In some embodiments, the alert signal is delivered to a user of the device and/or to a remote device, for example a remote computer, a remote server, and/or a remote cloud storage.

According to some exemplary embodiments, a relation between the acquired machine data and the stored instructions is determined at block 920, for example as part of a verification process to make sure that a machine used in the preparation of the bioactive compound operates according to the stored protocol for preparation of the bioactive compound. In some embodiments, if the relation between the acquired machine data and the stored protocol is not a desired relation, the verification is a negative verification, and an alert signal is delivered at block 903, for example as described in FIG. 9A. In some embodiments, the alert signal is delivered to a user of the device and/or to a user of the machine, and/or to a remote device, for example a remote computer, a remote server, and/or a remote cloud storage.

According to some exemplary embodiments, if the relation between the read ingredient ID and/or machine data and the stored protocol is a desired relation, then an indication is delivered at block 922. In some embodiments, the indication is delivered to a user of the ID verifying device, for example using a user interface of the ID verifying device. In some embodiments, the indication is a human detectable indication, which is optionally delivered visually and/or by sound.

Alternatively or additionally, the indication is delivered to a remote device. In some embodiments, only after receiving an indication that the determined relation is a desired relation, the ingredient is physically added to the mixture of ingredients during the preparation of the bioactive compound.

According to some exemplary embodiments, the ID verifying device determines if the bioactive compound preparation process is completed, at block 924, for example based on the protocol stored in the memory of the device.

According to some exemplary embodiments, if the preparation process is not complete, then the ID verifying device indicates that an additional ingredient ID and/or additional machine data needs to be read, at block 926. In some embodiments, the additional ingredient ID is an ID of an ingredient that follows the first ingredient in the stored preparation protocol. In some embodiments, the additional machine data is machine data that relates to an additional protocol step or a different operation of the machine, that follows the first machine data in the stored protocol. In some embodiments, a time window in which ID reading is disabled, or a time point for reading the additional ingredient ID from the time the previous ID was read, is set based on the stored protocol. Optionally, the time window or the time point is set based on a reaction time, for example a chemical reaction that needs to occur prior to physically adding the additional ingredient to the mixture of ingredients, mixing time of ingredients, and/or heating time of the ingredients mixture. In some embodiments, during the time window, for example the time window in which the ID reading is disabled, the ID verifying device does not allow reading of additional ingredients ID.

According to some exemplary embodiments, once an ID of an additional ingredient and/or machine data is read at block 926, the ID is verified at block 920, as previously described.

According to some exemplary embodiments, if the bioactive compound preparation is completed and/or is performed according to verified steps and verified ingredients based on the stored protocol, for example as determined at block 924, an indication is delivered at block 928. In some embodiments, the indication is a human detectable indication, for example a visual and/or a sound indication, delivered to a user of the ID verifying device. Alternatively or additionally, the indication is delivered to a remote device.

According to some exemplary embodiments, if the bioactive compound preparation is completed and/or is performed according to verified steps and verified ingredients based on the stored protocol, then a marker, for example a stamp of the ID verifying device is unlocked and/or is activated, at block 930. In some embodiments, the marker is activated electrically. In some embodiments, the marker is unlocked by changing a state of a lock, for example an electrical lock, from a locked position to an unlocked position. In some embodiments, the marker is unlocked by activating an actuator, for example to remove a physical blocker of the marker, for example a stamp. In some embodiments, the maker is also activated or is allowed to be activated in case some allowed modifications in at least one ingredient and/or at least one protocol step is performed.

According to some exemplary embodiments, an item associated with the bioactive compound is marked, for example physically marked, with a verification marking at block 932. In some embodiments, an item associated with the bioactive compound comprises a package of the bioactive compound, documentation associated with the bioactive compound, the bioactive compound, for example a tablet of the bioactive compound. In some embodiments, the documentation comprises a work order for manufacturing the bioactive compound, a drug prescription, a drug label or any other document associated with the bioactive compound. In some embodiments, the marking indicates that at least one modification in one or more of the ingredients and/or protocol steps was performed.

Exemplary Verification of a Tool Set Preparation Process

Figure 9C:
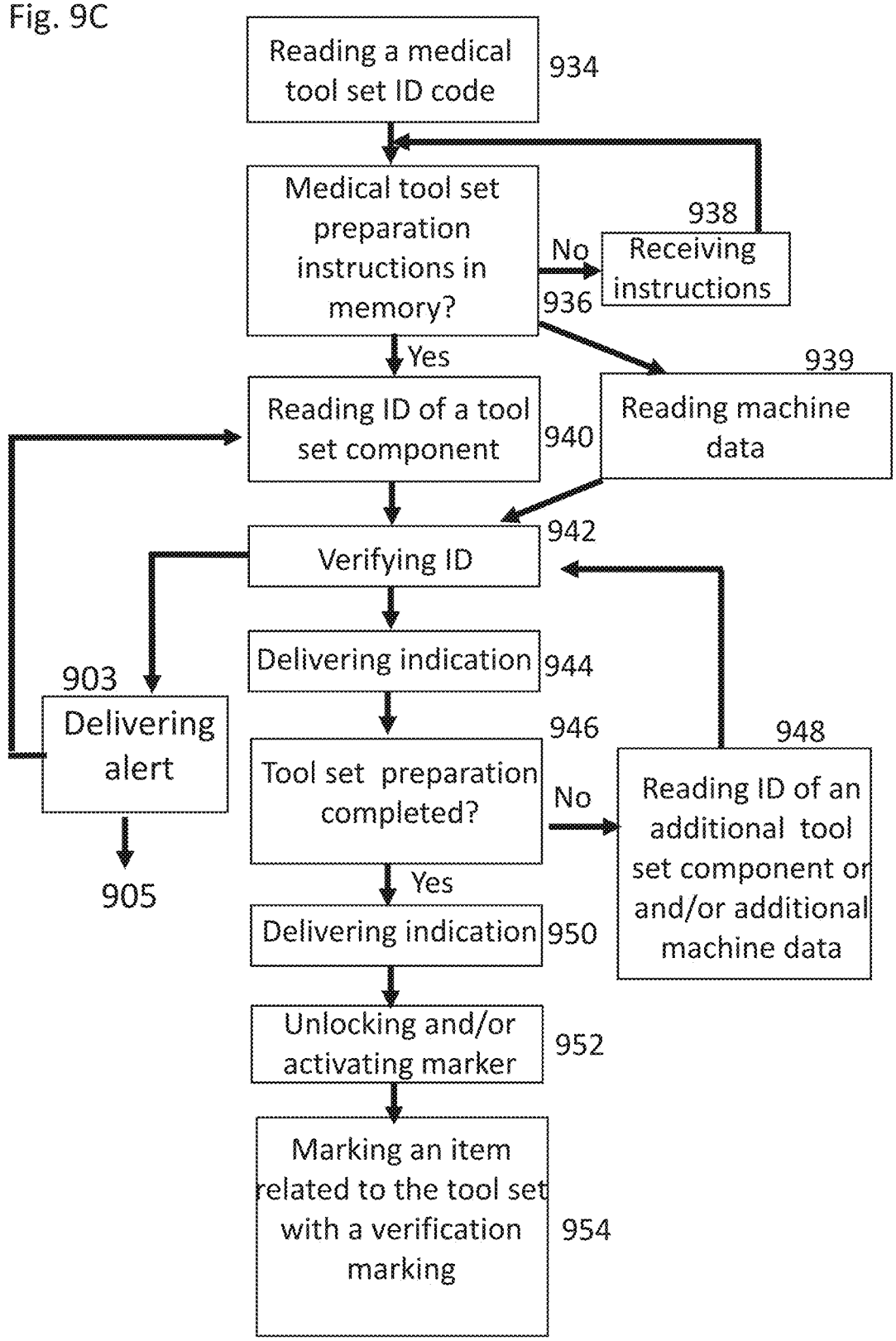
FIG. 9C is a flow chart of a process for preparation of a tool set, for example a medical tool set, according to some exemplary embodiments of the invention.

According to some exemplary embodiments, the ID verifying device is used to verify that a tool set, for example a medical tool set is prepared according to a desired protocol, according to a desired standard, for example an ISO standard, and/or to include a predetermined set of tools. In some embodiments, the tool set is a medical tool set that is prepared prior to a surgical procedure. In some embodiments, the ID verifying device is used to mark an item associated with a prepared tool set with a verification marking indicating that the tool set was prepared according to predetermined standards and/or following a desired protocol. Reference is now made to FIG. 9C depicting a process for verifying preparation of a tool set, for example a medical tool set, according to some exemplary embodiments of the invention.

According to some exemplary embodiments, a tool set ID, for example a medical tool set ID, is read at block 934. In some embodiments, the tool set ID is read prior to preparation or assembly of the medical tool set. In some embodiments, the ID code is read by an ID reader of the ID verifying device.

According to some exemplary embodiments, the ID verifying device determines a relation between the read ID code and information, for example instructions or a protocol of a procedure for preparation of the tool set, that are stored in the memory of the ID verifying device, at block 936. In some embodiments, if a protocol does not exist in the memory of the ID verifying device an indication is delivered to a user of the ID verifying device, for example using the user interface of the device. Additionally, if the protocol does not exist in the memory of the ID verifying device, at least some of the instructions are downloaded from a remote device, for example a remote computer, a remote server, a remote cloud storage, at block 938.

According to some exemplary embodiments, machine data is acquired at 939. In some embodiments, data from a machine, for example an external device that is used during the manufacturing of at least one tool of the tool set or a machine that is used for organizing the tool set, is acquired at block 939.

According to some exemplary embodiments, if instructions, for example a protocol for preparation of tool set exist in the memory of the ID verifying device, an indication is delivered to a user of the ID verifying device. Additionally or alternatively, a verifying process is initiated, for example by reading an ID of a component of the tool set, for example an ID of a tool to be included in the tool set, at block 940.

According to some exemplary embodiments, a relation between the acquired tool ID and the stored instructions is determined at block 942, for example as part of a verification process, to make sure that the tool associated with the tool ID is part of the protocol for preparation of the tool set. In some embodiments, if the relation between the acquired tool ID and the stored protocol is not a desired relation, the verification is a negative verification, and an alert signal is delivered at block 903, for example as described in FIG. 9A. In some embodiments, the alert signal is delivered to a user of the device and/or to a remote device, for example a remote computer, a remote server, and/or a remote cloud storage.

According to some exemplary embodiments, a relation between the acquired machine data and the stored instructions is determined at block 942, for example as part of a verification process to make sure that a machine used in the preparation of the tool set operates according to the stored protocol for preparation of tool set. In some embodiments, if the relation between the acquired machine data and the stored protocol is not a desired relation, the verification is a negative verification, and an alert signal is delivered at block 903, for example as described in FIG. 9A. In some embodiments, the alert signal is delivered to a user of the device and/or to a user of the machine, and/or to a remote device, for example a remote computer, a remote server, and/or a remote cloud storage.

According to some exemplary embodiments, if the relation between the acquired tool ID and the store protocol is a desired relation, then an indication is delivered at block 944. In some embodiments, the indication is delivered to a user of the ID verifying device, for example using a user interface of the ID verifying device. In some embodiments, the indication is a human detectable indication, which is optionally delivered visually and/or by sound. Alternatively or additionally, the indication is delivered to a remote device. In some embodiments, only after receiving an indication that the determined relation is a desired relation, the tool associated with the tool ID is physically added to the prepared tool set.

According to some exemplary embodiments, the ID verifying device determines if the tool set preparation is completed, at block 946, for example based on the protocol stored in the memory of the device.

According to some exemplary embodiments, if the preparation process is not complete, then the ID verifying device indicates that an additional tool ID and/or additional machine data, needs to be read, at block 948. In some embodiments, the additional tool ID is an ID of a tool that needs to be added to the prepared tool set following the previously added tool. In some embodiments, the additional machine data is machine data that relates to an additional protocol step or a different operation of the machine, that follows the first machine data in the stored protocol.

According to some exemplary embodiments, once an ID of an additional tool is read at block 948, the ID is verified at block 942, as previously described.

According to some exemplary embodiments, if the tool set preparation is completed and/or is performed according to verified steps and verified tools based on the stored protocol, for example as determined at block 942, an indication is delivered at block 950. In some embodiments, the indication is a human detectable indication, for example a visual and/or a sound indication, delivered to a user of the ID verifying device. Alternatively or additionally, the indication is delivered to a remote device.

According to some exemplary embodiments, if the tool set preparation is completed and/or is performed according to verified steps and using verified tools based on the stored protocol, then a marker, for example a stamp of the ID verifying device is unlocked and/or is activated, at block 952. In some embodiments, the marker is activated electrically. In some embodiments, the marker is unlocked by changing a state of a lock, for example an electrical lock, from a locked position to an unlocked position. In some embodiments, the marker is unlocked by activating an actuator, for example to remove a physical blocker of the marker. According to some exemplary embodiments, an item associated with the tool set is marked, for example physically marked, with a verification marking at block 954. In some embodiments, an item associated with the tool set comprises a package of the tool set, documentation associated with the tool set, the tool set, and/or at least one tool of the tool set. In some embodiments, the documentation comprises a work order for preparation of the tool set, a label of the tool set or any other document associated with the tool set. In some embodiments, the marking indicates that at least one allowed modification in one or more of the tools arrangement and/or protocol steps was performed.

Exemplary Verification of a Cleaning Procedure

According to some exemplary embodiments, the ID verifying device is used to verify that a cleaning procedure, for example a sterilization procedure, is performed according to a desired protocol and/or according to desired standards, for example ISO standards, or any other standard generated by a regulatory authority. In some embodiments, the ID verifying device is used to mark an item, for example a document associated with the cleaning procedure with a marking indicating that the cleaning procedure was performed according to an approved protocol and/or under approved conditions. Reference is now made to FIG. 9D, depicting a process for verification of a cleaning, for example a sterilization procedure, according to some exemplary embodiments of the invention.

According to some exemplary embodiments, a cleaning procedure ID code is acquired, for example read at block 956. In some embodiments, the ID code is acquired prior to initiation of the cleaning procedure associated with the ID code. In some embodiments, the ID code is read by an ID reader of the ID verifying device.

According to some exemplary embodiments, the ID verifying device determines a relation between the acquired ID code and information, for example instructions, for example a protocol of the cleaning procedure, that are stored in the memory of the ID verifying device, at block 958. In some embodiments, if a protocol of the cleaning procedure does not exist in the memory of the ID verifying device, an indication is delivered to a user of the ID verifying device, for example using the user interface of the device. Additionally, if the protocol does not exist in the memory of the ID verifying device, at least some of the protocol or instructions are downloaded from a remote device, for example a remote computer, a remote server, a remote cloud storage, at block 960.

According to some exemplary embodiments, if instructions, for example a protocol of the cleaning procedure exist in the memory of the ID verifying device, an indication is delivered to a user of the ID verifying device. Additionally or alternatively, a verifying process is initiated, for example by reading an ID of a component of the cleaning procedure, for example an ID of a cleaning material, at block 962.

According to some exemplary embodiments, machine data is acquired at 959. In some embodiments, data from a machine, for example an external device that is used during the cleaning process, for example a sterilization process, is acquired at block 939. In some embodiments, the machine comprises an autoclave, a floor washing machine, a dish washer and/or a sterilization device.

According to some exemplary embodiments, a relation between the acquired cleaning procedure ID component and the stored instructions is determined at block 964, for example as part of a verification process to make sure that the cleaning procedure component associated with the component ID is part of the cleaning procedure protocol. In some embodiments, if the relation between the acquired component ID and the stored protocol is not a desired relation, the verification is a negative verification, and an alert signal is delivered at block 903, for example as described in FIG. 9A. In some embodiments, the alert signal is delivered to a user of the device and/or to a remote device, for example a remote computer, a remote server, and/or a remote cloud storage.

According to some exemplary embodiments, a relation between the acquired machine data and the stored instructions is determined at block 964, for example as part of a verification process to make sure that the machine works according to the cleaning procedure protocol. In some embodiments, if the relation between the acquired machine data and the stored protocol is not a desired relation, the verification is a negative verification, and an alert signal is delivered at block 903, for example as described in FIG. 9A. In some embodiments, the alert signal is delivered to a user of the device and/or to a remote device, for example a remote computer, a remote server, and/or a remote cloud storage.

According to some exemplary embodiments, if the relation between the acquired cleaning procedure component ID and/or the acquired machine data, and the stored protocol is a desired relation, then an indication is delivered at block 966. In some embodiments, the indication is delivered to a user of the ID verifying device, for example using a user interface of the ID verifying device. In some embodiments, the indication is a human detectable indication, which is optionally delivered visually and/or by sound. Alternatively or additionally, the indication is delivered to a remote device. In some embodiments, only after receiving an indication that the determined relation is a desired relation, the cleaning component associated with the component ID is used in the cleaning procedure.

According to some exemplary embodiments, the ID verifying device determines if the cleaning procedure is completed, at block 968, for example based on the protocol stored in the memory of the device.

According to some exemplary embodiments, if the cleaning procedure is not complete, then the ID verifying device indicates that an additional cleaning procedure component ID and/or additional machine data needs to be acquired, for example read, at block 970. In some embodiments, the additional cleaning procedure component ID is an ID of a cleaning procedure component that follows the first cleaning procedure component in the stored procedure protocol. In some embodiments, the additional machine data is machine data that follows the previously acquired machine data in the stored procedure protocol. In some embodiments, a time window in which ID reading is disabled, or a time point for reading the additional ID from the time the previous ID was read, is set based on the stored protocol. Optionally, the time window or the time point is set based on a reaction time, for example a chemical reaction and/or a physical action for example wiping or rinsing, that needs to occur prior to physically adding, using or performing the additional cleaning procedure component. In some embodiments, during the time window, for example the time window in which the ID reading is disabled, the ID verifying device does not allow reading of additional IDs.

According to some exemplary embodiments, once an ID of an additional cleaning procedure component is acquired, for example read at block 970, the ID is verified at block 964, as previously described.

According to some exemplary embodiments, if the cleaning procedure is complete and/or is performed according to verified steps and verified cleaning procedure components based on the stored protocol, for example as determined at block 964, an indication is delivered at block 972. In some embodiments, the indication is a human detectable indication, for example a visual and/or a sound indication, delivered to a user of the ID verifying device. Alternatively or additionally, the indication is delivered to a remote device.

According to some exemplary embodiments, if the cleaning procedure is complete and/or is performed according to verified steps and verified components based on the stored protocol, then a marker, for example a stamp of the ID verifying device is unlocked and/or is activated, at block 974. In some embodiments, the marker is activated electrically. In some embodiments, the marker is unlocked by changing a state of a lock, for example an electrical lock, from a locked position to an unlocked position. In some embodiments, the marker is unlocked by activating an actuator, for example to remove a physical blocker of the marker, for example a stamp. According to some exemplary embodiments, an item associated with the cleaning procedure is marked, for example physically marked, with a verification marking at block 976. In some embodiments, an item associated with the cleaning procedure comprises documentation associated with the cleaning procedure, a label or a sign. In some embodiments, the documentation comprises a work order for performing the cleaning procedure, or any other document associated with the cleaning procedure. In some embodiments, the marking indicates that at least one allowed modification in one or more of the cleaning ingredients and/or cleaning protocol steps was performed.

It is expected that during the life of a patent maturing from this application many relevant ID readers configured to read an ID indication, a 2D or a 3D code will be developed; the scope of the term ID reader is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for identity (ID) verification in a medical facility, by verifying a relation between a patient ID indication and an ID indication of a medical-related item using a handheld verifying device, comprising:
    reading a first ID indication of a patient and a second ID indication of a medical-related item within a selected acquiring time window, stored in a memory associated with the medical handheld verifying device;
    storing in a memory of said handheld verifying device said first ID, and said second ID indication;
    verifying by said handheld verifying device, a desired relation between the first ID indication and the second ID indication by said medical handheld verifying device, wherein said verifying comprises verifying that said medical-related item is associated with said patient, wherein said verifying is prevented if said reading is not performed within said selected acquiring time window;
    delivering an indication with results of said verifying.

2. A method according to claim 1, wherein said delivering comprises transmitting an electronic verification signal to a remote device according to results of said verifying.

3. A method according to claim 2, wherein said transmitting comprises transmitting an alert signal to said remote device if said desired relation is not verified.

4. A method according to claim 2, wherein said transmitted electronic verification signal includes identification information of a user of said handheld verifying device, wherein said user is a physician or a medical personnel.

5. A method according to claim 2, wherein said transmitted verification signal includes information about a physician or a medical personnel performing said storing.

6. A method according to claim 1, comprising:
    reading at least one of, said first ID indication and said second ID indication, prior to said storing.

7. A method according to claim 1, wherein said delivering comprises, delivering, following said verifying, a human detectable indication by a user interface of said handheld verifying device, if said desired relation is verified.

8. A method according to claim 1, wherein said delivering comprises,
    delivering, following said verifying, an alert signal by a user interface of said handheld verifying device, if said desired relation is not verified.

9. A method according to claim 1, wherein said medical related item comprises at least one of, a patient sample, test results, patient treatment, a drug and/or patient location.

10. A method according to claim 1, wherein said second ID indication comprises an indication related to a bio-active agent, and wherein said verifying comprises verifying that said bio-active agent is prescribed to said patient based on said verification of said desired relation.

11. A method according to claim 1, comprising authenticating an ID of a user of said handheld verifying device.

12. A method according to claim 1, wherein said verifying is performed if a distance between said first ID indication and said second ID indication is shorter than 1 meter.

13. A handheld verifying device, comprising:
    a memory storing ID information of a medical personnel using the device, and for storing of ID indications, wherein said ID indications comprise at least one ID indication of a patient and at least one ID indication of a medical-related item;
    an identification (ID) reader configured to read said at least one ID indication of said patient and said at least one ID indication of said medical-related item;
    a communication circuitry configured to transmit a signal to a remote device;
    a control circuitry, wherein said control circuitry is configured to verify a relation between said at least one first ID indication and said at least one second ID indication of said medical-related item, and to signal said communication circuitry to transmit said signal to said remote device with results of said verifying and with said stored ID information of said medical personnel using said device, wherein said verifying a relation by said control circuitry comprises verifying that said medical-related item is associated with said patient, wherein said control circuitry is configured to prevent said verifying if said reading by said ID reader is not performed within a selected acquiring time window stored in said memory.

14. A device according to claim 13, wherein said at least one ID indication of said medical-related item stored in said memory comprises an indication of at least one of, patient sample, bio-active agent, test results, patient treatment and/or patient location.

15. A device according to claim 13, comprising a user interface configured to generate a human detectable indication, wherein said control circuitry is configured to signal said user interface to generate a positive human detectable indication if said verified relation is a desired relation, or an alert human detectable indication if said verified relation is not a desired relation.

16. A device according to claim 13, wherein said remote device comprises at least one of, a mobile device, a remote computer, a remote server and/or a cloud storage.

17. A device according to claim 13, wherein said ID reader comprises an optical sensor configured to acquire an image of one or more of said ID indications.

18. A device according to claim 13, wherein said ID reader comprises a barcode reader or a 3D code reader.

19. A device according to claim 13, wherein said device is shaped and size to be held by a single hand of an adult subject.

20. A device according to claim 13, comprising a user ID verifying module electrically connected to said control circuitry, configured to read at least one biometric parameter of a user of the ID verifying device indicating user identity and/or permission of said user to use the ID verifying device.

\* \* \* \* \*